United States Patent
Fürstner et al.

(10) Patent No.: US 8,431,724 B2
(45) Date of Patent: Apr. 30, 2013

(54) IEJIMALID ANALOGA AND USES THEREOF

(75) Inventors: Alois Fürstner, Mülheim an der Ruhr (DE); Christina Nevado-Blàzquez, Zürich (CH); Mario Waser, Leonding (AT); Emilie Moulin, Strasbourg (FR); Christophe Aïssa, Liverpool (GB)

(73) Assignee: Studiengesellschaft Kohle mbH, Mulheim der Ruhr (DE)

( * ) Notice: Subject to any disclaimer, the term of this patent is extended or adjusted under 35 U.S.C. 154(b) by 333 days.

(21) Appl. No.: 12/532,524

(22) PCT Filed: Mar. 5, 2008

(86) PCT No.: PCT/DE2008/000400
§ 371 (c)(1),
(2), (4) Date: Nov. 20, 2009

(87) PCT Pub. No.: WO2008/113320
PCT Pub. Date: Sep. 25, 2008

(65) Prior Publication Data
US 2010/0056616 A1    Mar. 4, 2010

(30) Foreign Application Priority Data
Mar. 22, 2007   (DE) .................... 10 2007 013 765

(51) Int. Cl.
*C07D 313/04*    (2006.01)

(52) U.S. Cl.
USPC ........................................................ 549/271

(58) Field of Classification Search .................... 549/271
See application file for complete search history.

(56) References Cited

FOREIGN PATENT DOCUMENTS
JP      02 042075        2/1990
JP      02042075     *   2/1990

OTHER PUBLICATIONS

Pedersen et al. Journal of American Chemical Society, 2001, 123, 9738-9742.*
Dorwald F. A. Side Reactions in Organic Synthesis, 2005, Wiley: VCH, Weinheim p. IX of Preface p. 1-15.*
Venkatesh et al., J. Pharm. Sci. 89, 145-54 (2000) (p. 146, left column).*
Furstner A. et al. Journal of American Chemical Society, 2007, 129, 9150-9161.*
Schweitzer et al. Bioorganic & Medicinal Chemistry (2007), 15(9),3208-3216.*
A. Fürstner et al; "Total Synthesis of Iejimalide A-D and Assesment of the Remarkable Actin-Depolymerizing Capacity of These Polyene Macrolides"; J. Am. Chem. Soc., 2007, 129, pp. 9150-9161.
D. Schweitzer et al; "Synthesis of carbamate derivatives of iejimalides. Retention of normal antiproliferative activity and localization of binding in cancer cells"; Bioorganic & Medicinal Chemistry 15, 2007, pp. 3208-3216.
Kobayashi, "Isolation of 24-memberedmacrolides from sea squirt (*Eudistoma rigida*) and their anticancer activity"; Chemical Abstract Services 1990.
Kobayashi, et al; "Iejimalides A and B, Novel 24-Membered Macrolides with Potent Antileukemic Activity from the Okinawan Tunicate *Eudistoma cf. rigida*"; J. Org. Chem. 1988, 53, pp. 6147-6150.
Kikuchi et al; "Iejimalides C and D, New Antineoplastic 24-Membered Macrolide Sulfates from the Okinawan Marine Tunicate *Eudistoma cf rigida*"; Tetrahedron Letters, 1991, vol. 32, No. 6, pp. 797-798.
Nozawa et al; "Absolute stereochemistry and antitumor activity of iejimalides"; Bioorganic & Medicinal Chemistry 14, 2006, pp. 1063-1067.
Tsuda et al; "Stereochemistry of iejimalide B": Tetrahedron Letters 44, 2003, pp. 1395-1399.
Kazami et al; "Iejimalides Show Anti-Osteroclast Activity via V-ATPase Inhibition": Biosci. Biotechnol. Biochem, 70, 6, 2006, pp. 1364-1370.
Fürstner et al; "Total synthesis of Iejimalide B"; Angew. Chem. Int. Ed., 2006, 45, pp. 5837-6842.
Fürstner, et al; "Studies on Iejimalide B: Preparation of the Seco Acid and Identification of the Molecule's "Achilles Heel""; Angew. Chem. Int. Ed., 2006, 45, pp. 5832-5837.
Cottard, et al; "Synthesis of a Major Subunit of the Iejimalides"; Tetrahedron Letters, 1995, vol. 36, No. 18, pp. 3115-3118.
Mendlik et al; "Stereocontrolled Synthesis of the C(1)-C(11) Subunit of the Iejimalides"; Tetrahedron Letters, 1997, vol. 38, No. 36, pp. 6375-6378.
Pedersen, et alL; "Enantioconvergent synthesis by sequential asymmetric Horner-Wadsworth-Emmons and Palladium-catalyzed allylic substitution reactions"; J. Am. Chem. Soc. 2001, 123, pp. 9738-9742.
Gagnepain et al., "Molecular Editing and Assessment of the Cytotoxic Properties of Iejimalide and Progeny", Chem. Eur. J., (2011), 17: p. 6973-6984.

* cited by examiner

*Primary Examiner* — Nizal Chandrakumar
(74) *Attorney, Agent, or Firm* — Norris McLaughlin & Marcus, P.A.

(57) ABSTRACT

The invention relates to Iejimalides having the following formula (I) in which a, b, c, d, e, f, g, h, i, j, k, l, m, n, o, p are simple or double bonds, the continuous lines representing at least one simple bond, the dotted lines representing a possible bond. A double bond can be present but it is not necessary, and provided that a continuous line is also present, or a simple bond can be present if no other line is represented; m=0-20 and n1-n18=1, 2. The bonds can be used as chemotherapeutic agents for treating cancer.

7 Claims, 10 Drawing Sheets a) DIBAL-H, CH$_2$Cl$_2$, -78°C, 95%; b) MnO$_2$, CH$_2$Cl$_2$; c) Pd(OAc)$_2$, PPh$_3$, Et$_2$Zn, THF, -78°C - -20°C, 71% (2 steps); d) TBAF, THF, 89%; e) PivCl, DMAP, pyridine, 94%; f) Cp$_2$ZrHCl, THF; g) I$_2$, THF, 81% (2 steps); h) LiHBEt$_3$, THF, 82%.

a) PdCl$_2$(dppf), Ba(OH)$_2$, DMF, 70%; b) EDC HCl, PyrrPy, CH$_2$Cl$_2$, 78%; c) 16 (20%), CH$_2$Cl$_2$, 75%.

a) TBAF, THF; b) 17, EDC, HOBt, NMM, CH$_2$Cl$_2$, 75% (2 steps); c) TBAF, THF; d) 19, EDC, HOBt, NMM, CH$_2$Cl$_2$; e) TBAF, THF, 20% (3 steps); f) TBAF, THF; g) 21, Et$_3$N, CH$_2$Cl$_2$, 45% (2 steps).

a) MnO₂, CH₂Cl₂, 95%; b )(-)Ipc₂BOMe, Allyl-Mg-Br, Et₂O, -78°C, 75%;
c) Me₃OBF₄, Protonsponge, CH₂Cl₂, 88%.

a) DIBAL-H, CH$_2$Cl$_2$; b) 29, LiHMDS, THF; c) PhSSPh, AIBN, THF, 85 °C, 77% (3 steps);
d) DDQ, CH$_2$Cl$_2$, H$_2$O (5%); e) Dess-Martin, CH$_2$Cl$_2$; f) CHI$_3$, CrCl$_2$, Dioxane/THF (6:1), 46% (3 steps);
g) 27, Ph$_2$PO$_2$NBU$_4$, CuTC, Pd(PPh$_3$)$_4$, DMF; h) LiOH, THF, MeOH, 68% (2 steps).

a) PhZnCl, Pd(PPh$_3$)$_4$, THF, 50°C, 76%; b) DDQ, CH$_2$Cl$_2$, H$_2$O (5%); c) Dess-Martin, CH$_2$Cl$_2$; d) CHI$_3$, CrCl$_2$, Dioxane/THF (6:1), 45% (3 steps); e) 27, Ph$_2$PO$_2$NBU$_4$, CuTC, Pd(PPh$_3$)$_4$, DMF, 79%; f) Me$_3$SnOH, DCE, 80°C, 56%.

g) 27, Ph$_2$PO$_2$NBU$_4$, CuTC, Pd(PPh$_3$)$_4$, DMF, 86%; h) LiOH, MEOH, THF, 90%.

a) 35, DCC, PyrrPy, CH$_2$Cl$_2$, 26%; b) 16 (20%), CH$_2$Cl$_2$, 74%; c) TBAF, THF, 24%;
d) 37, DCC, PyrrPy, CH$_2$Cl$_2$, 73%; e) 16 (20%), CH$_2$Cl$_2$, 69%; f) TBAF, THF, 85%.

IEJIMALID ANALOGA AND USES THEREOF

This application is a 371 of PCT/DE2008/000400, filed 5 Mar. 2008, which claims foreign priority benefit under 35 U.S.C. §119 of the German Patent Application No. DE 10 2007 013 765.8, filed 22 Mar. 2007.

The present invention relates to compounds having the structure (1), wherein $R_1$-$R_{18}$, A, B, C, D, a-p and $X_1$-$X_4$ are as defined herein, the synthesis thereof and the use of these compounds in actin-binding and apopthosis assays.

BACKGROUND OF THE INVENTION

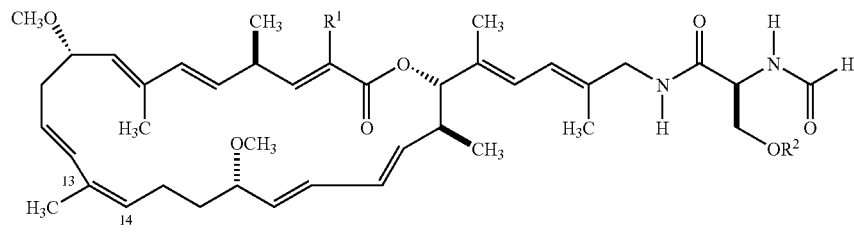

Iejimalides A-D

Iejimalide A (1), $R^1 = R^2 = H$
Iejimalide B (2), $R^1 = Me, R^2 = H$
Iejimalide C (3), $R^1 = H, R^2 = SO_3Na$
Iejimalide D (4), $R^1 = Me, R^2 = SO_3Na$ are natural substances first isolated from the tunicate *Eudistoma* cf. *rigida* collected off Ie island, Okinawa province, Japan. ((a) J. Kobayashi, J. Cheng, T. Ohta, H. Nakamura, S. Nozoe, Y. Hirata, Y. Ohizumi, T. Sasaki, *J. Org. Chem.* 1988, 53, 6147-6150; (b) Y. Kikuchi, M. Ishibashi, T. Sasaki, J. Kobayashi, *Tetrahedron Lett.* 1991, 32, 797-798). It was only after a re-extraction from a *Cystodytes* sp. that enough material was accumulated to allow for the establishment of their relative and absolute stereochemistry; at the same time, the configuration of the C13-C14 double bond was corrected to (Z) rather than (E) as originally assigned (a) K. Nozawa, M. Tsuda, H. Ishiyama, T. Sasaki, T. Tsuruo, J. Kobayashi, *Bioorg. Med. Chem.* 2006, 14, 1063-1067; (b) M. Tsuda, K. Nozawa, K. Shimbo, H. Ishiyama, E. Fukushi, J. Kawabata, J. Kobayashi, *Tetrahedron Lett.* 2003, 44, 1395-1399).

Specifically, the dataset for iejimalide A disclosed in 2005 by the National Cancer Institute (NCI) illustrates the truly remarkable potency of 1 against the panel of 60 standard human cancer cell lines, with $GI_{50}$ and TGI values in the low nanomolar range. (The activity data are available from the NCI homepage (http://www.dtp.nci.nih.gov/docs/dtp_search.html) and although the NCI data show no particular selectivity, a preliminary report from the Walther Cancer Research Center (http://www.nd.edu/~science/documents/waltherbrochure.pdf) claims spectacular effects against colon cancer and stunning morphological changes upon injection of iejimalides into solid tumors. Equally remarkable is Kobayashi's report that the activity profile of 1-4 does not correlate with that of other anticancer drugs, which might indicate an unprecedented mode of action. The same authors also demonstrated the potent in vivo activity of 3 and 4 against P388 leukemia.

More recently, Iejimalides have been identified as potent osteoclasts inhibitors. (Kazami, S.; Muroi, M.; Kawatani, M.; Kubota, T.; Usui, T.; Kobayashi, J.; Osada, H. Biosci. Biotechnol. Biochem. 2006, 70 (6), 1364-1370.) Since it is known that osteoclasts are sensitive to vacuolar $H^+$-ATPase (V-ATPase) inhibitors, it was shown that Iejimalides inhibited the V-ATPases of both mammalian and yeast cells in situ, and of yeast V-ATPases in vitro. A bafilomycin-resistant yeast mutant conferred Iejimalides resistance, suggesting that IEJLs target a site similar to the bafilomycins/concanamycins-binding site.

In spite of this data collection, the cellular targets for Iejimalides remain unknown. However, fluorescent labelling studies showed that they do not accumulate in the nucleus, but in the cytoplasm. Also microtubule binding or disruption seem not to be the mode of action of this compounds. (Schweitzer, D.; Zhu, J.; Jarori, G.; Tanaka, J.; Higa, T.; Davisson, V. J.; Helquist, P., Bioorg. Med. Chem. 2007, 15(9), 3208-3216)

Collectively, these data suggest that the Ijimalides may be candidates for further development in a (pre)clinical setting. Since they can only be isolated from natural sources in scarce amounts, a synthetic campaign in our group has revealed the first total synthesis of Iejimalide B, presumably the most active member of the family in enough amounts for further biological tests. (a) Fürstner, A.; Nevado, C.; Tremblay, M.; Chevrier, C.; Teply, F.; Aïssa, C.; Waser, M. *Angew. Chem. Int. Ed.* 2006, 45, 5837-5842. b) Fürstner, A.; Aïssa, C.; Chevrier, C.; Teply, F.; Nevado, C.; Tremblay, M. *Angew. Chem. Int. Ed.* 2006, 45, 5832-5837, and a) M. Cottard, N. Kann, T. Rein, B. Åkermark, P. Helquist, Tetrahedron Lett. 1995, 36, 3115-3118; b) M. T. Mendlik, M. Cottard, T. Rein, P. Helquist, Tetrahedron Lett. 1997, 38, 6375-6378; c) T. M. Pedersen, E. L. Hansen, J. Kane, T. Rein, P. Helquist, P.-O. Norrby, D. Tanner, J. Am. Chem. Soc. 2001, 123, 9738-9742.)

What is needed are flexible methods for producing analoga of Iejimalides (A-D) and analoga thereof and of "libraries" of analoga of Iejimalides (A-D) that exhibit superior pharmacological properties (activity, selectivity, stability) and therefore show advantages in the use as anticancer therapeutic agent, cytostatika, V-ATPase inhibitor and in the binding to the actin cytoscleton or in dysfunction of the actin cytoscleton.

SUMMARY OF THE INVENTION

Figure 1:
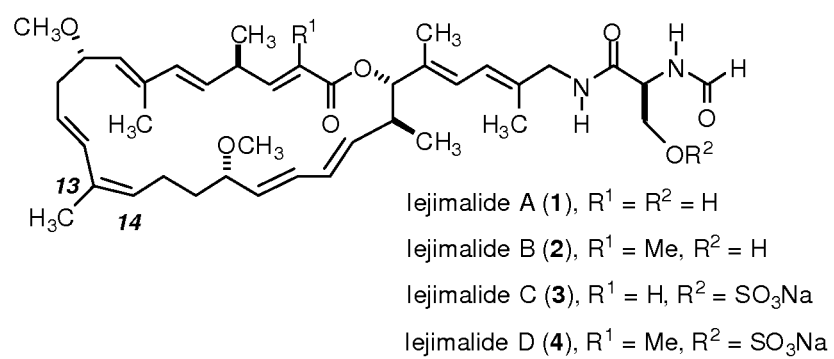
FIG. 1 depicts structures of Iejimalide A (1), Iejimalide B (2), Iejimalide C (3), and Iejimalide D (4).

The present invention relates to analoga of Iejimalides A-D and provides novel synthetic methodologies enabling access to analoga with a broad range of structural diversity that permit structure-activity studies in detail to address the cellular targets of these molecules and its use as therapeutic medicines.

1) General Description of Compounds of the Invention

The present invention provides compounds of general formula (I):

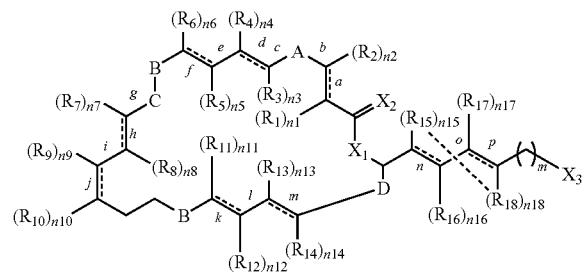

wherein:

a, b, c, d, e, f, g, h, i, j, k, l, m, n, o, p are single or double bonds;

the continuous line _____ represents at least a single bond, the dotted line - - - represents a possible bond, whereby a double bond can be present although not necessarily if there is also a continuous line, or a single bond can be present when no other line is present;

where m=0-20;

where $n_1$ to $n_{18}$=1, 2;

each occurrence of $R_x$, (x=1-18), is independently, hydrogen, halogen, an aliphatic, heteroaliphatic, aryl, heteroaryl, or alkylheteroaryl moiety, or $OR_a$, wherein $R_a$ is hydrogen, a protecting group, or an aliphatic, heteroaliphatic, aryl, heteroaryl, alkylaryl or alkylheteroaryl moiety, or $Si(R_b)_3$, wherein each occurrence of $R_b$ is independently hydrogen, halogen, an aliphatic, heteroaliphatic, aryl, heteroaryl, alkylaryl, or alkylheteroaryl moiety;

$R_{15}$ and $R_{18}$ together represent CH=CH, N=$CR_c$, S—$CR_c$, O—$CR_c$, $CR_c$=$CR_d$ wherein $R_c$ is hydrogen, halogen, a protecting group, an aliphatic, heteroaliphatic, aryl, heteroaryl, alkylaryl or alkylheteroaryl moiety and $R_d$ is hydrogen, halogen, a protecting group, or an aliphatic, heteroaliphatic, aryl, heteroaryl, or alkylheteroaryl moiety;

$X_1$ is O, S or $N(R_e)_2$, wherein each occurrence of $R_e$ is, independently, hydrogen, or lower alkyl;

$X_2$ is O, S or $NR_f$, wherein $R_f$ is hydrogen, a protecting group, an aliphatic, heteroaliphatic, aryl, heteroaryl, alkylaryl, alkylaryl or alkylheteroaryl moiety, or $OR_g$, wherein $R_g$ is hydrogen, a protecting group, an aliphatic, heteroaliphatic, aryl, heteroaryl, alkylaryl, or alkylheteroaryl moiety;

$X_3$ is $OR_h$, $SR_h$, $N(R_h)_2$ wherein each occurrence of $R_h$ is independently hydrogen, a protecting group, a natural aminoacid, and unnatural aminoacid, —$OR_i$, —$SR_i$, $C(O)OR_i$, $C(O)N(R_i)_2$, $SO_2R_i$, $O(C=O)R_i$, $NR_i(C=O)R_i$, $C(O)R_i$, $C(O)OR_i$, $C(O)N(R_i)_2$, $OCO_2R_i$, or an aliphatic, heteroaliphatic, aryl, heteroaryl, alkylaryl, or alkylheteroaryl moiety, wherein each occurrence of $R_i$ is independently hydrogen, a protecting group, or an aliphatic, heteroaliphatic, aryl, heteroaryl, alkylaryl, or alkylheteroaryl moiety;

A, C is independently $CH_2$, $CHR_j$, $C(R_j)_2$, =$CR_j$, wherein each occurrence of $R_j$ is, independently hydrogen, halogen, a protecting group, an aliphatic, heteroaliphatic, aryl, heteroaryl, alkylaryl, or alkylheteroaryl moiety, or $OR_k$, or $N(R_k)_2$ or $SR_k$ wherein each occurrence of $R_k$ is, independently, hydrogen, a protecting group, an aliphatic, heteroaliphatic, aryl, heteroaryl, alkylaryl, or alkylheteroaryl moiety;

Each occurrence of B and D is independently $CH_2$, $CHR_l$, $C(R_l)_2$, wherein each occurrence of $R_j$ is independently hydrogen, halogen, a protecting group, an aliphatic, heteroaliphatic, aryl, heteroaryl, alkylaryl, or alkylheteroaryl moiety, or $OR_m$, or $N(R_m)_2$ or $SR_m$ wherein each occurrence of $R_m$ is, independently, hydrogen, a protecting group, an aliphatic, heteroaliphatic, aryl, heteroaryl, alkylaryl, or alkylheteroaryl moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted, cyclic or acyclic, or branched or unbranched;

whereby each of the foregoing stereocenters present in the structure or in the substituents are independently R, S or mixtures of R and S in any proportion (not only, but could also be racemic);

Embodiments of this invention are subject to one or more, or all of the following limitations:

(1) If - - - with _____ represents a double bond, then $n_x$=1, for the $R_x$ substituents directly attached to this bond.

(2) If A is =CRj, and b is a double bond, then a is a single bond, n1=2 and n2=1.

(3) If a is a double bond, then $n_1$=1, $n_2$=1, b is a single bond, and A cannot be =CRj (4) If A is =CRj, and c is a double bond, then $n_3$=1, and b and d are single bonds.

(5) If d is a double bond, then $n_3$=1, $n_4$=1, c and e are single bonds and A cannot be =CRj (6) If e is a double bond, then $n_4$=1, $n_6$=1, d and f are single bonds and $n_8$=2.

(7) If f is a double bond, then $n_5$=1 and $n_6$=1 and e is a single bond.

(8) If g is a double bond, C is =CRj, and then $n_7$=1 and h is a single bond.

(9) If h is a double bond, then $n_7$=1, $n_8$=1, and g and i are single bonds.

(10) If i is a double bond, then $n_8$=1, $n_9$=1, and h and j are single bonds.

(11) If j is a double bond, then $n_9=1$, $n_{10}=1$, and i is a single bond.

(12) If k is a double bond, then $n_{11}=1$, $n_{12}=1$, and l is a single bond.

(13) If l is a double bond, then $n_{12}=1$, $n_{13}=1$, and k and m are single bonds.

(14) If m is a double bond, then $n_{13}=1$, $n_{14}=1$, and l is a single bond.

(15) If n is a double bond, then $n_{15}=1$, $n_{16}=1$, and o is a single bond.

(16) If o is a double bond, then $n_{16}=1$, $n_{17}=1$, and n and p are single bonds.

(17) If p is a double bond, then $n_{17}=1$, $n_{18}=1$, and o is a single bond.

(18) If - - - represents a single bond, then $R_{16}$ and $R_{18}$ together represent CH=CH, N=$CR_c$, S—$CR_c$, O—$CR_c$, $CR_c$=$CR_d$ wherein $R_c$ is hydrogen, halogen, a protecting group, or an aliphatic, heteroaliphatic, aryl, heteroaryl, alkylaryl or alkylheteroaryl moiety and $R_d$ is hydrogen, halogen, a protecting group, or an aliphatic, heteroaliphatic, aryl, heteroaryl, alkylaryl or alkylheteroaryl moiety;

The following embodiments are excluded from this invention:

1) Compounds of formula (I) in certain embodiments do not include compounds wherein the following occur simultaneously: if $X_1$ is O (S configuration), $X_2$ is O, $R_1$=Me, a is a double bond, $R_2$=H, A=$CHCH_3$ (R configuration), d is a double bond, $R_3$=$R_4$=H, $R_5$=Me, f is double bond, $R_6$=H, B is CHOMe (S configuration), C is $CH_2$, h is a double bond, $R_7$=$R_8$=H, $R_9$=Me, j is a double bond, $R_{10}$=H, B is CHOMe (S configuration), k is a double bond, $R_{11}$=$R_{12}$=$R_{13}$=$R_{14}$=H, m is a double bond, D is $CHCH_3$ (S configuration), $R_{15}$=Me, n is a double bond, $R_{16}$=$R_{17}$=H, p is a double bond, $R_{18}$=Me, m=1, and $X_3$ is NHCOOtBu or:

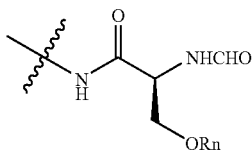

wherein Rn=H, OTBS, CONHRo, wherein $R_0$ is phenyl, 2-napthyl, —$(CH_2)_5$-2-O-napthyl, 2-coumaryl, or $SO_3X_4$ wherein $X_4$ is Na;

2) Compounds of formula (I) in certain embodiments do not include compounds wherein the following occurs simultaneously: if $X_1$ is O (S configuration), $X_2$ is O, $R_1$=H, a is a double bond, $R_2$=H, A=$CHCH_3$ (R configuration), d is a double bond, $R_3$=$R_4$=H, $R_5$=Me, f is double bond, $R_6$=H, B is CHOMe (S configuration), C is $CH_2$, h is a double bond, $R_7$=$R_8$=H, $R_9$=Me, j is a double bond, $R_{10}$=H, B is CHOMe (S configuration), k is a double bond, $R_{11}$=$R_{12}$=$R_{13}$=$R_{14}$=H, m is a double bond, D is $CHCH_3$ (S configuration), $R_{15}$=Me, n is a double bond, $R_{16}$=$R_{17}$=H, p is a double bond, $R_{18}$=Me, m=1, and $X_3$ is:

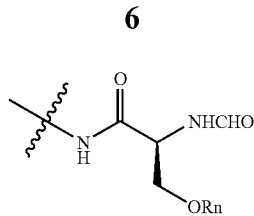

wherein Rn=H, CONHRo, wherein Ro is phenyl, 2-napthyl, —$(CH_2)_5$-2-O-napthyl, 2-coumaryl, or $SO_3X_4$ wherein $X_4$ is Na;

2) Featured Classes of Compounds

It will be appreciated that for compounds as generally described above, certain classes of compounds are of special interest.

2.1 For example, one class of compounds of special interest includes those compounds having the structure of formula (I) in which $X_1$ and $X_2$ are each O, and the compound has the structure:

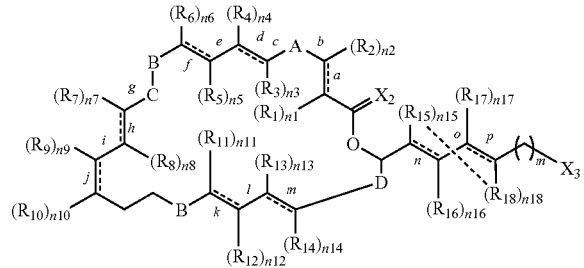

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.2 Another class of compounds of special interest consists of compounds having the structure of formula (I) in which $X_1$ is NRe and $X_2$ is O, and the compound has the structure:

and $R_{1-18}$, A-D, a-p, are as defined above and in subclasses herein. It will be appreciated that in certain embodiments of this class of compounds one or more of, or all of the aforementioned limitations (1)-(18) apply.

2.3 Another class of compounds of special interest consists of compounds having the structure of formula (I) in which a is a double bond and the compound has the structure:

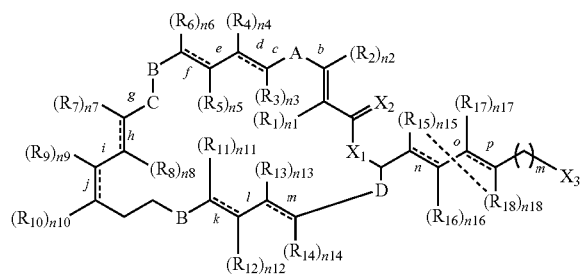

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.4 Another class of compounds of special interest consists of compounds having the structure of formula (I) in which a is a single bond and the compound has the structure:

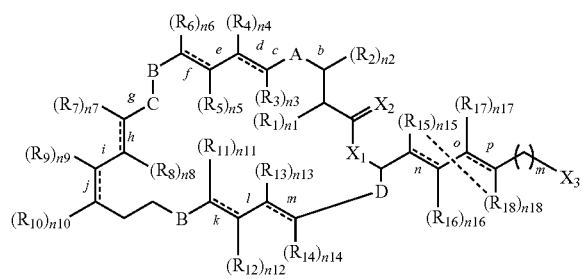

and $R_{1-18}$, A-D, a-p, are as defined above and in subclasses herein. It will be appreciated that in certain embodiments of this class of compounds one or more of, or all of the aforementioned limitations (1)-(18) apply.

2.5 Another class of compounds of special interest consists of compounds having the structure of formula (I) in which b is a double bond, and the compound has the structure:

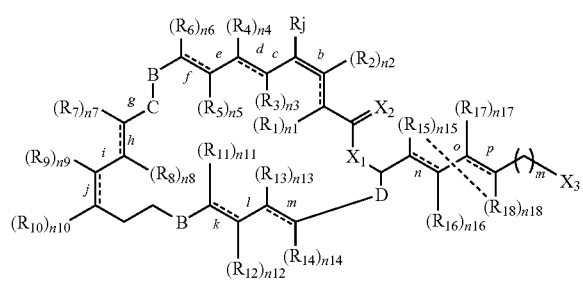

and $R_{1-18}$, A-D, a-p, are as defined above and in subclasses herein. It will be appreciated that in certain embodiments of this class of compounds one or more of, or all of the aforementioned limitations (1)-(18) apply.

2.6 Another class of compounds of special interest consists of compounds having the structure of formula (I) in which b is a single bond, and the compound has the structure:

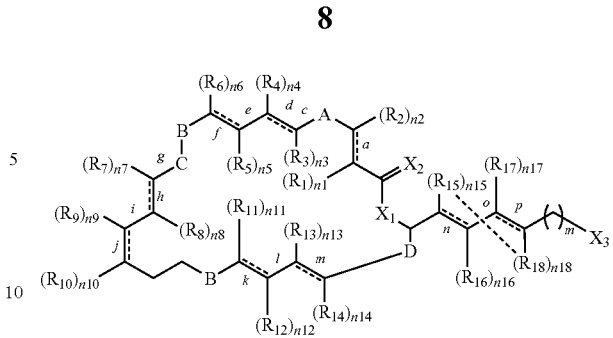

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.7 Another class of compounds of special interest consists of compounds having the structure of formula (I) in which c is a double bond, and the compound has the structure:

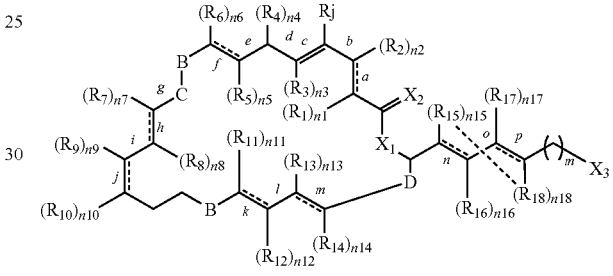

and $R_{1-18}$, A-D, a-p, are as defined above and in subclasses herein. It will be appreciated that in certain embodiments of this class of compounds one or more of, or all of the aforementioned limitations (1)-(18) apply.

2.8 Another class of compounds of special interest consists of compounds having the structure of formula (I) in which c is a single bond, and the compound has the structure:

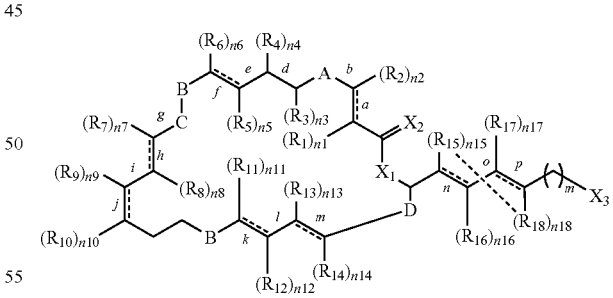

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.9 Another class of compounds of special interest consists of compounds having the structure of formula (I) in which d is a double bond, and the compound has the structure:

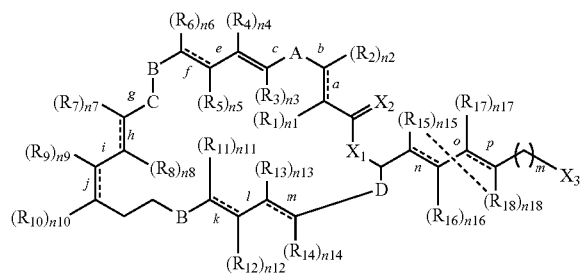

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.10 Another class of compounds of special interest consists of compounds having the structure of formula (I) in which d is a single bond, and the compound has the structure:

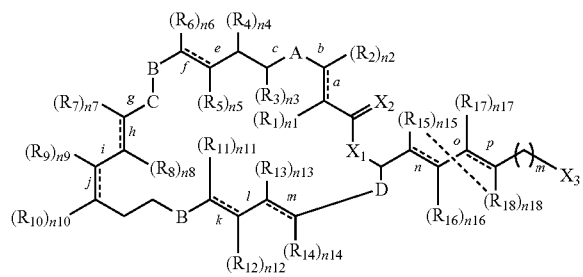

and $R_{1-18}$, A-D, a-p, are as defined above and in subclasses herein. It will be appreciated that in certain embodiments of this class of compounds one or more of, or all of the aforementioned limitations (1)-(18) apply.

2.11 Another class of compounds of special interest consists of compounds having the structure of formula (I) in which e is a double bond, and the compound has the structure:

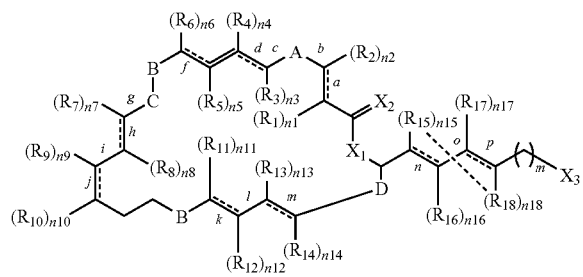

and $R_{1-18}$, A-D, a-p, are as defined above and in subclasses herein. It will be appreciated that in certain embodiments of this class of compounds one or more of, or all of the aforementioned limitations (1)-(18) apply.

2.12 Another class of compounds of special interest consists of compounds having the structure of formula (I) in which e is a single bond, and the compound has the structure:

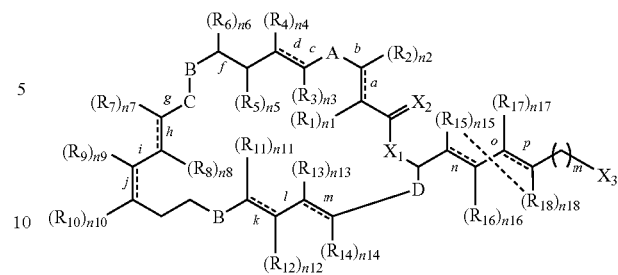

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.13 Another class of compounds of special interest consists of compounds having the structure of formula (I) in which f is a double bond, and the compound has the structure:

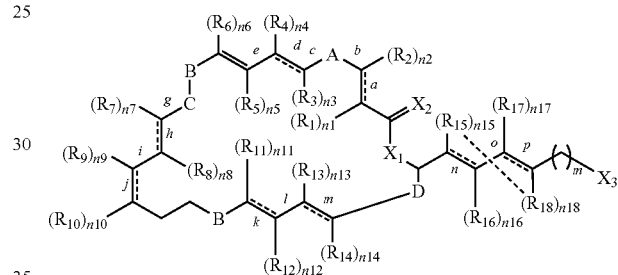

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.14 Another class of compounds of special interest consists of compounds having the structure of formula (I) in which f is a single bond, and the compound has the structure:

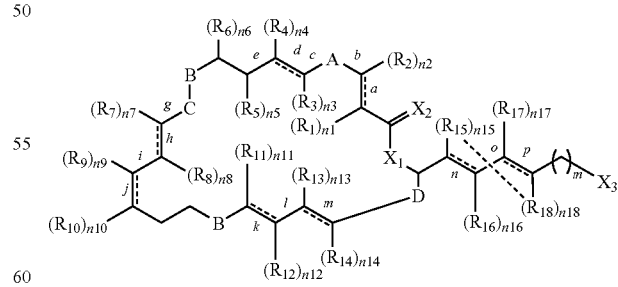

and $R_{1-18}$, A-D, a-p, are as defined above and in subclasses herein. It will be appreciated that in certain embodiments of this class of compounds one or more of, or all of the aforementioned limitations (1)-(18) apply.

2.15 Another class of compounds of special interest consists of compounds having the structure of formula (I) in which g is a double bond, and the compound has the structure:

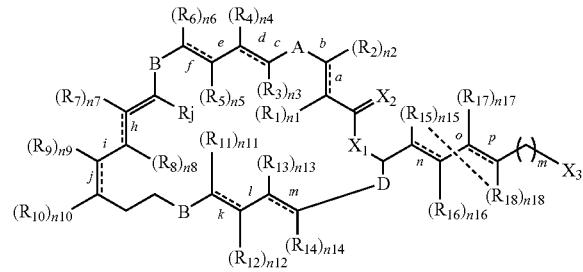

and $R_{1-18}$, A-D, a-p, are as defined above and in subclasses herein. It will be appreciated that in certain embodiments of this class of compounds one or more of, or all of the aforementioned limitations (1)-(18) apply.

2.16 Another class of compounds of special interest consists of compounds having the structure of formula (I) in which g is a single bond, and the compound has the structure:

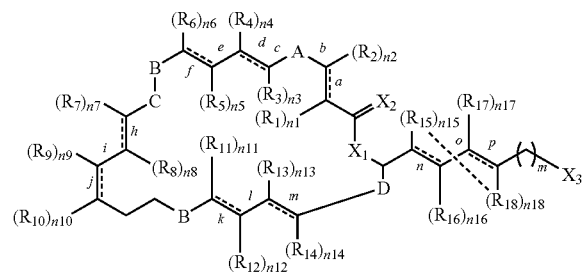

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.17 Another class of compounds of special interest consists of compounds having the structure of formula (I) in which h is a double bond, and the compound has the structure:

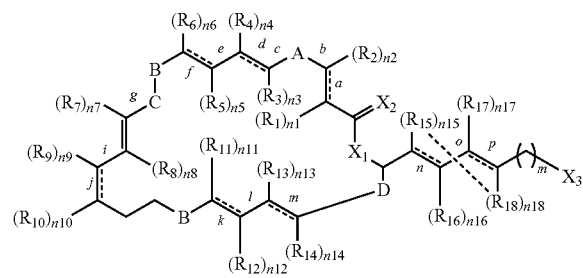

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.18 Another class of compounds of special interest consists of compounds having the structure of formula (I) in which h is a single bond, and the compound has the structure:

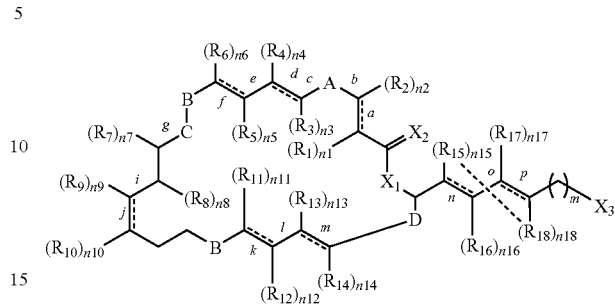

and $R_{1-18}$, A-D, a-p, are as defined above and in subclasses herein. It will be appreciated that in certain embodiments of this class of compounds one or more of, or all of the aforementioned limitations (1)-(18) apply.

2.19 Another class of compounds of special interest consists of compounds having the structure of formula (I) in which i is a double bond, and the compound has the structure:

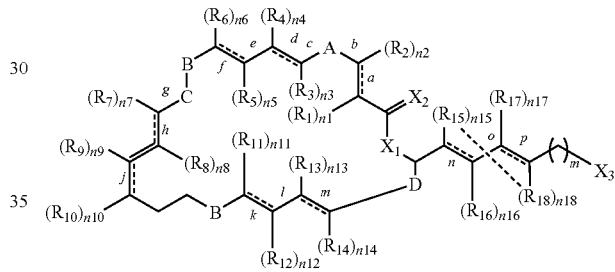

and $R_{1-18}$, A-D, a-p, are as defined above and in subclasses herein. It will be appreciated that in certain embodiments of this class of compounds one or more of, or all of the aforementioned limitations (1)-(18) apply.

2.20 Another class of compounds of special interest consists of compounds having the structure of formula (I) in which i is a single bond, and the compound has the structure:

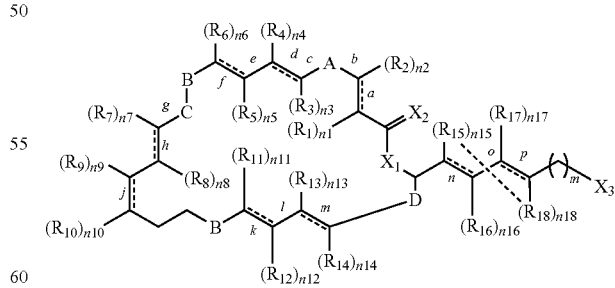

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.21 Another class of compounds of special interest consists of compounds having the structure of formula (I) in which j is a double bond, and the compound has the structure:

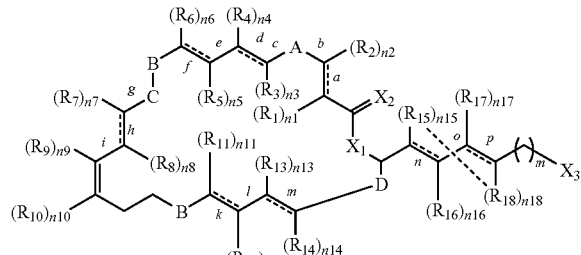

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.22 Another class of compounds of special interest consists of compounds having the structure of formula (I) in which j is a single bond, and the compound has the structure:

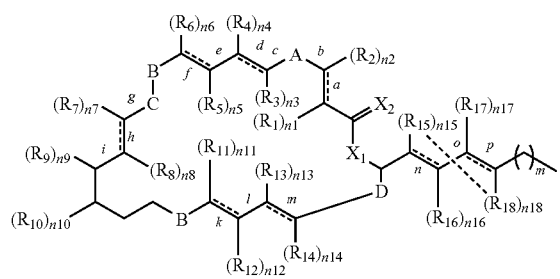

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply 2.23 Another class of compounds of special interest consists of compounds having the structure of formula (I) in which k is a double bond, and the compound has the structure:

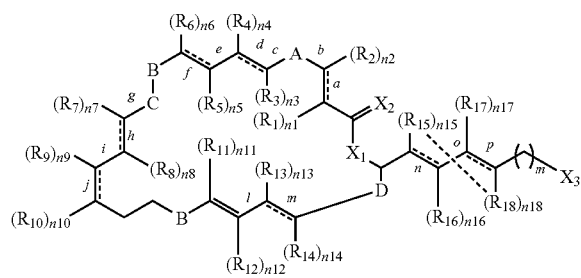

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.24 Another class of compounds of special interest consists of compounds having the structure of formula (I) in which k is a single bond, and the compound has the structure:

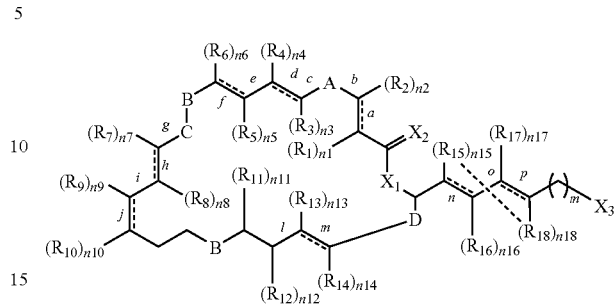

and $R_{1-18}$, A-D, a-p, are as defined above and in subclasses herein. It will be appreciated that in certain embodiments of this class of compounds one or more of, or all of the aforementioned limitations (1)-(18) apply.

2.25 Another class of compounds of special interest consists of compounds having the structure of formula (I) in which l is a double bond, and the compound has the structure:

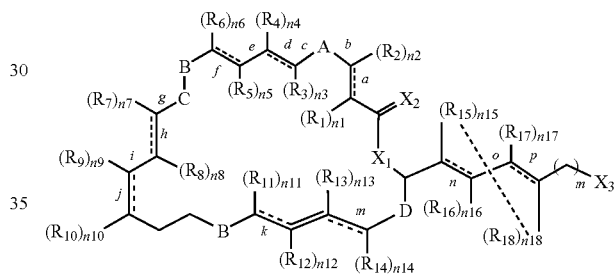

and $R_{1-18}$, A-D, a-p, are as defined above and in subclasses herein. It will be appreciated that in certain embodiments of this class of compounds one or more of, or all of the aforementioned limitations (1)-(18) apply.

2.26 Another class of compounds of special interest consists of compounds having the structure of formula (I) in which l is a single bond, and the compound has the structure:

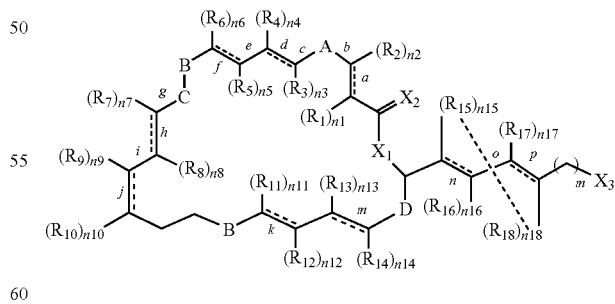

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.27 Another class of compounds of special interest consists of compounds having the structure of formula (I) in which m is a double bond, and the compound has the structure:

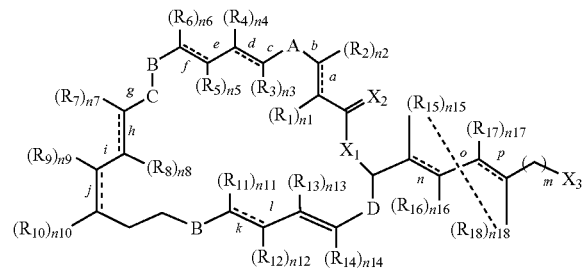

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.28 Another class of compounds of special interest consists of compounds having the structure of formula (I) in which m is a single bond, and the compound has the structure:

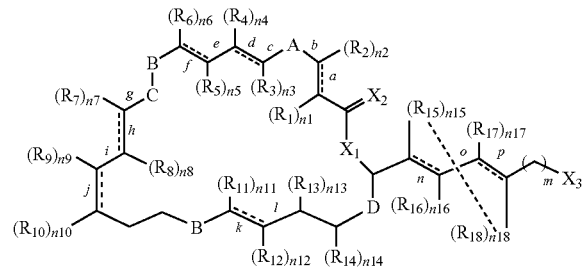

and $R_{1-18}$, A-D, a-p, are as defined above and in subclasses herein. It will be appreciated that in certain embodiments of this class of compounds one or more of, or all of the aforementioned limitations (1)-(18) apply.

2.29 Another class of compounds of special interest consists of compounds having the structure of formula (I) in which n is a double bond, and the compound has the structure:

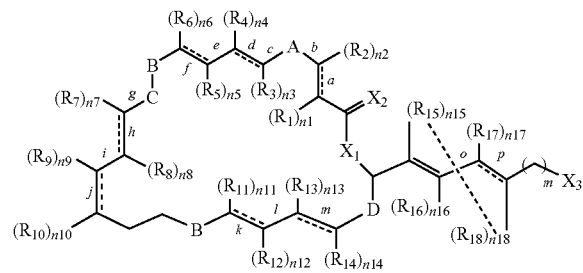

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.30 Another class of compounds of special interest consists of compounds having the structure of formula (I) in which n is a single bond, and the compound has the structure:

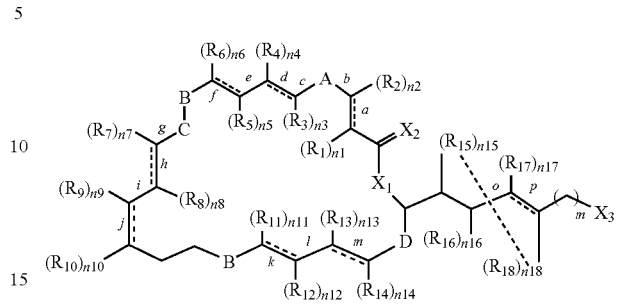

and $R_{1-18}$, A-D, a-p, are as defined above and in subclasses herein. It will be appreciated that in certain embodiments of this class of compounds one or more of, or all of the aforementioned limitations (1)-(18) apply.

2.31 Another class of compounds of special interest consists of compounds having the structure of formula (I) in which o is a double bond, and the compound has the structure:

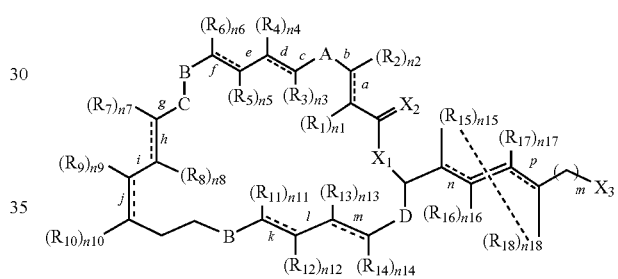

and $R_{1-18}$, A-D, a-p, are as defined above and in subclasses herein. It will be appreciated that in certain embodiments of this class of compounds one or more of, or all of the aforementioned limitations (1)-(18) apply.

2.32 Another class of compounds of special interest consists of compounds having the structure of formula (I) in which o is a single bond, and the compound has the structure:

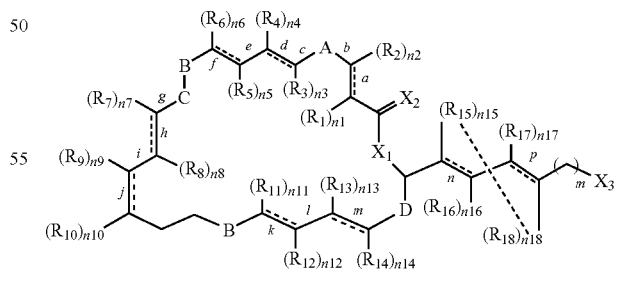

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.33 Another class of compounds of special interest consists of compounds having the structure of formula (I) in which p is a double bond, and the compound has the structure:

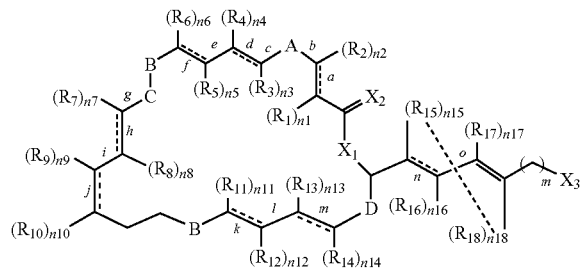

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.34 Another class of compounds of special interest consists of compounds having the structure of formula (I) in which p is a single bond, and the compound has the structure:

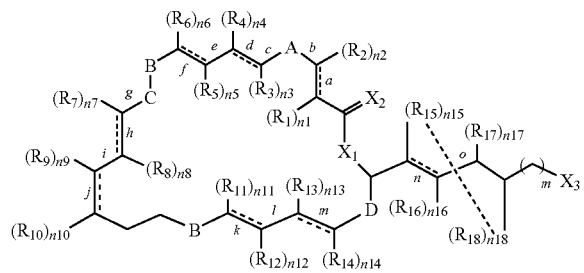

and $R_{1-18}$, A-D, a-p, are as defined above and in subclasses herein. It will be appreciated that in certain embodiments of this class of compounds one or more of, or all of the aforementioned limitations (1)-(18) apply.

2.35 Another class of compounds of special interest consists of compounds having the structure of formula (I) in which A represents —C(H)(Me)- and the compound has the structure:

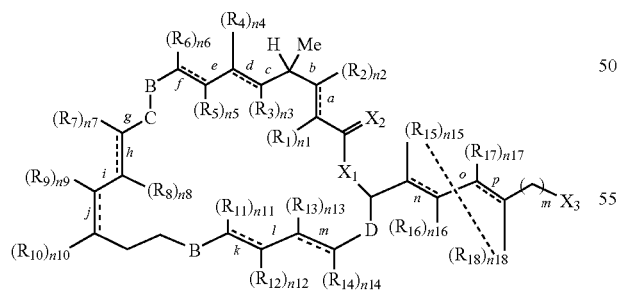

and $R_{1-18}$, B-D, a-p, are as defined above and in subclasses herein. It will be appreciated that in certain embodiments of this class of compounds one or more of, or all of the aforementioned limitations (1)-(18) and exclusions 1) and 2) apply.

2.36 Another class of compounds of special interest consists of compounds having the structure of formula (I) in which each occurrence of B, independently, represents —C(H)(OMe)- and the compounds have the structure:

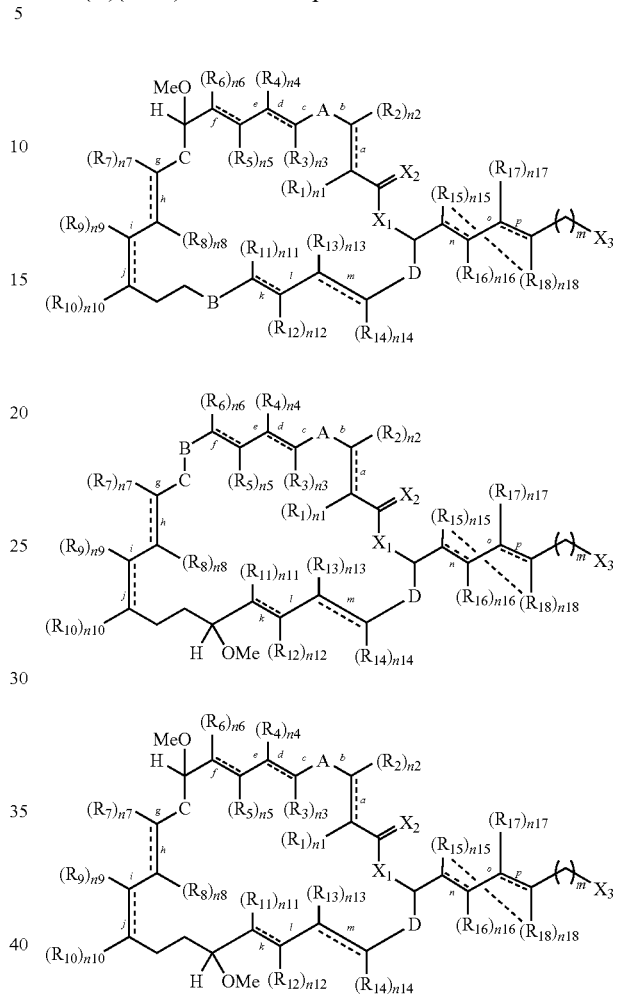

and $R_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.37 Another class of compounds of special interest consists of compounds having the structure of formula (I) in which C represents —CH$_2$— and the compounds have the structure:

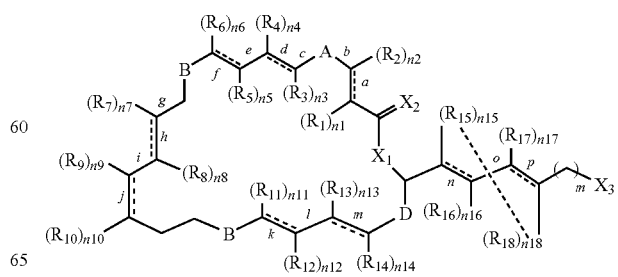

and R$_{1-18}$, A, B, D, a-p, are as defined above and in subclasses herein. It will be appreciated that in certain embodiments of this class of compounds one or more of, or all of the aforementioned limitations (1)-(18) and exclusions 1) and 2) apply.

2.38 Another class of compounds of special interest consists of compounds having the structure of formula (I) in which D represents —C(H)(Me)- and the compounds have the structure:

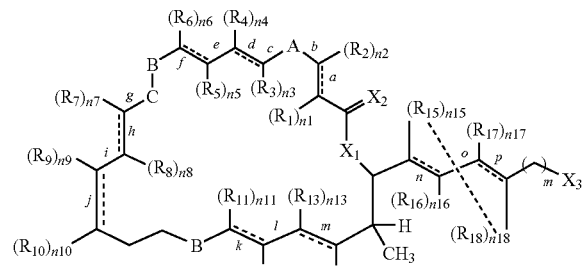

and R$_{1-18}$, A, B, C, a-p, are as defined above and in subclasses herein. It will be appreciated that in certain embodiments of this class of compounds one or more of, or all of the aforementioned limitations (1)-(18) and exclusions 1) and 2) apply.

2.39 Another class of compounds of special interest consists of compounds having the structure of formula (I) in which m=1 and X$_3$ represents —N(H)aminoacid- wherein the aa represents any natural aminoacid, and unnatural aminoacid and the compounds have the structure:

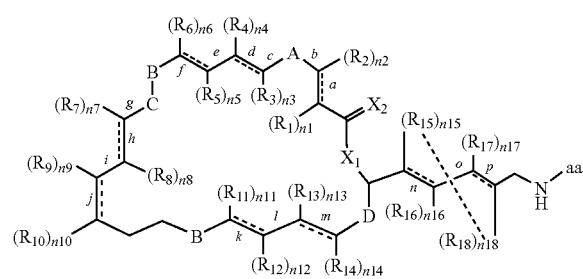

and R$_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.40 Another class of compounds of special interest consists of compounds having the structure of formula (I) in which X$_3$ represents —N(H)serine- wherein each occurrence of R$_n$ is, independently, hydrogen, a protecting group, a natural aminoacid, and unnatural aminoacid, —OR$_i$, —SR$_i$, C(O)OR$_i$, C(O)N(R$_i$)$_2$, SO$_2$R$_i$, O(C=O)R$_i$, NR$_i$(C=O)R$_i$, C(O)R$_i$, C(O)OR$_i$, C(O)N(R$_i$)$_2$, OCO$_2$R$_i$, or an aliphatic, heteroaliphatic, aryl, heteroaryl, alkylaryl, or alkylheteroaryl moiety, wherein each occurrence of R$_i$ is independently hydrogen, a protecting group, or an aliphatic, heteroaliphatic, aryl, heteroaryl, alkylaryl, or alkylheteroaryl moiety, and the products have the structure:

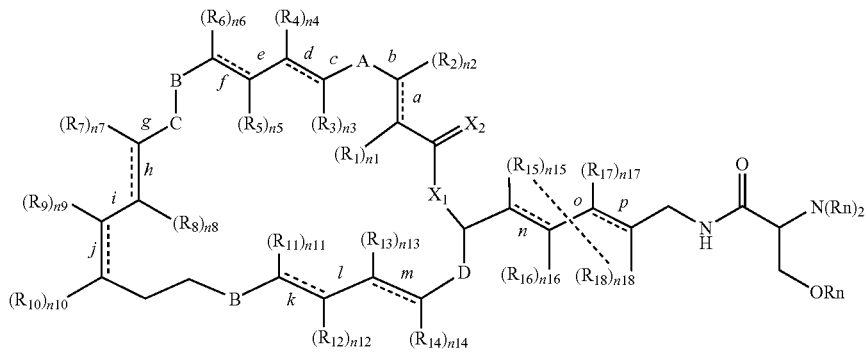

and R$_{1-18}$, A-D, a-p, are as defined above and in subclasses herein. It will be appreciated that in certain embodiments of this class of compounds one or more of, or all of the aforementioned limitations (1)-(18) and exclusions 1) and 2) apply.

2.41 Another class of compounds of special interest consists of compounds having the structure of formula (I) in which R$_{15}$ and R$_{18}$ simultaneously represent —CRc=CRd- and the products have the structure:

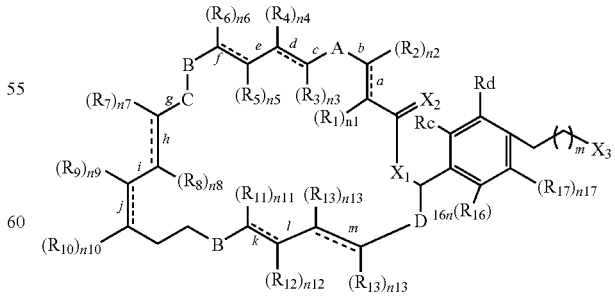

and R$_{1-18}$, A-D, a-p, are as defined above and in subclasses herein. It will be appreciated that in certain embodiments of this class of compounds one or more of, or all of the aforementioned limitations (1)-(18) apply.

The following structures illustrate several exemplary types of compounds of these classes. Others will be readily apparent to the reader:
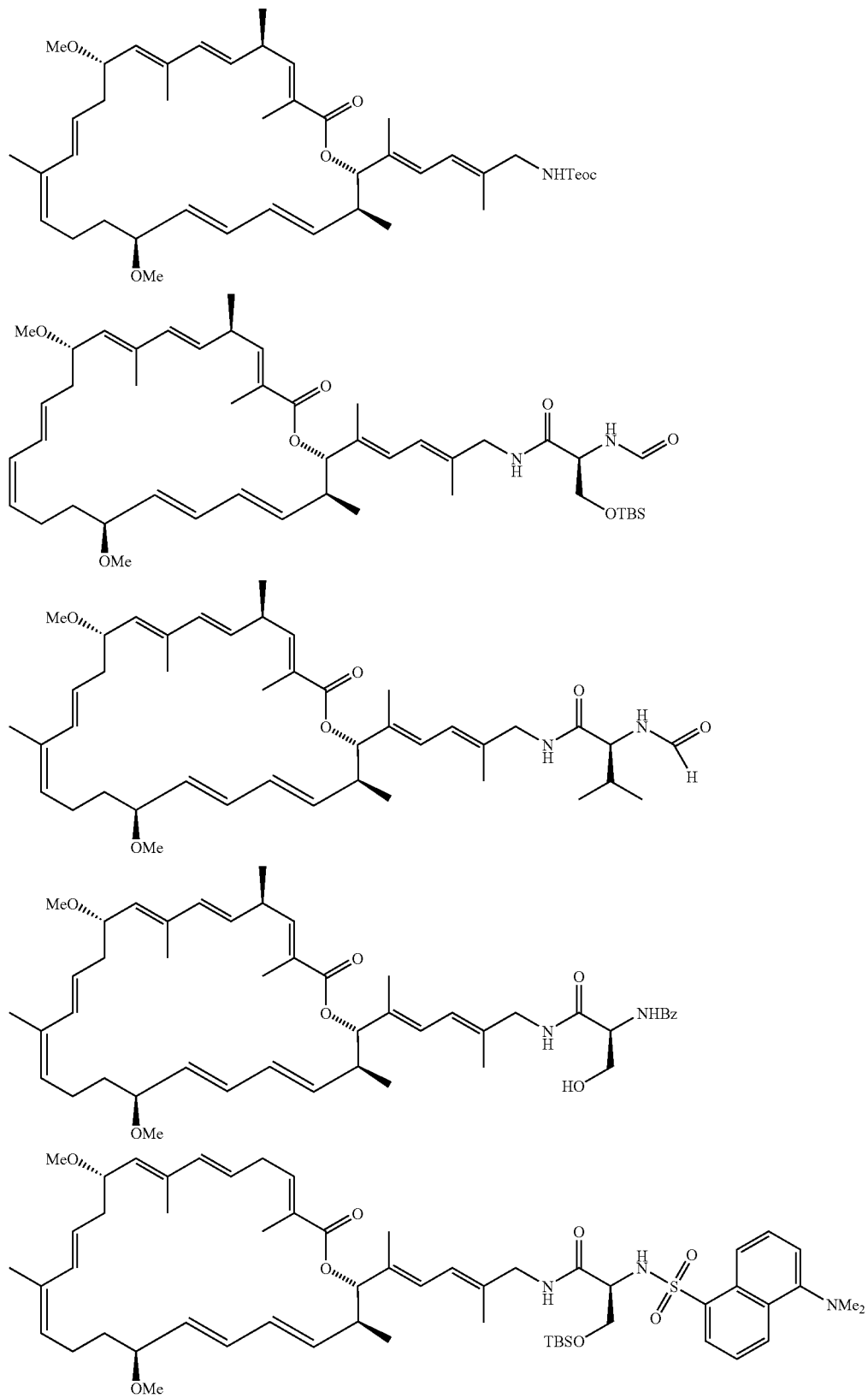

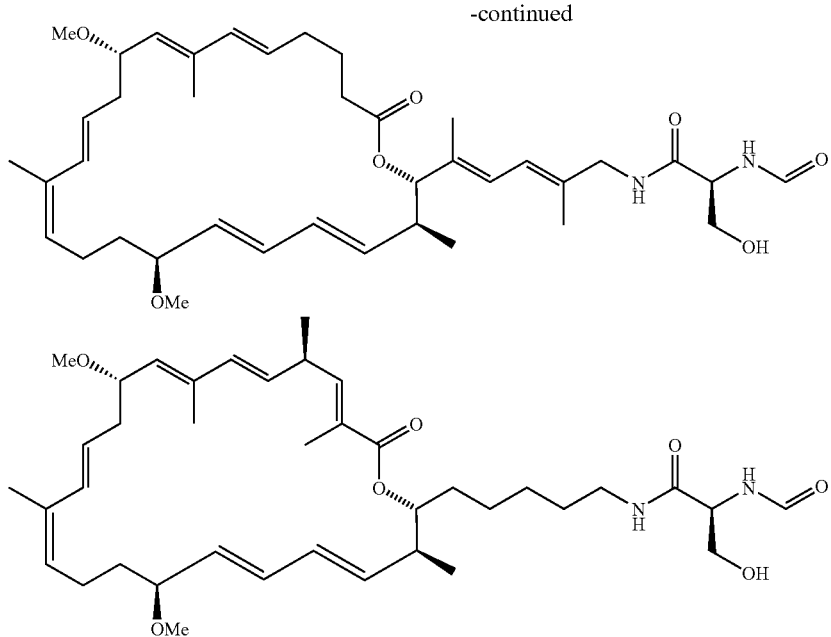

The foregoing compounds comprise one or more asymmetric centers, and thus can exist in various isomeric forms, e.g., stereoisomers and/or diastereoisomers. Thus, inventive compounds thereof may be in the form of an individual enantiomer, diastereomer or geometric isomer, or may be in the form of a mixture of stereoisomers.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers.

3) Compounds and Definitions 3.1) Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein.

Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Furthermore, it will be appreciated by one of ordinary skill in the art that the synthetic methods, as described herein, utilize a variety of protecting groups. By the term "protecting group", as used herein, it is meant that a particular functional moiety, e.g., C, O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

3.2) It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent.

When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer, actin-binding tests etc. . . . . . The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

3.3) The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 16 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the. alkyl, alkenyl, and alkynyl groups employed in the invention contain 1-4 carbon atoms.

Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

3.4) Some examples of substituents of the above-described aliphatic (and other) moieties of compounds of the invention include, but are not limited to aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, F, Cl, Br, I, —OH, —$NO_2$, —CN, —$CF_3$, —$CH_2CF_3$, —$CHCl_2$, —$CH_2OH$, —$CH_2CH_2OH$, —$CH_2NH_2$, —$CH_2SO_2CH_3$, —C(O)Rx, —$CO_2$(Rx), —CON(Rx)$_2$, —OC(O)Rx, —$OCO_2$Rx, —OCON(Rx)$_2$, —N(Rx)$_2$, —S(O)$_2$Rx, —NRx(CO)Rx wherein each occurrence of Rx independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the examples that are described herein.

3.5) In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl and the like.

3.6) It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, F, Cl, Br, I, —OH, —$NO_2$, —CN, —$CF_3$, —$CH_2CF_3$, —$CHCl_2$, —$CH_2OH$; —$CH_2CH_2OH$; —$CH_2NH_2$; —$CH_2SO_2CH_3$; —C(O)Rx; —$CO_2$(Rx); —CON(Rx)$_2$; —OC(O)Rx; —$OCO_2$Rx, —OCON(Rx)$_2$, —N(Rx)$_2$, —S(O)$_2$Rx; —NRx(CO)Rx wherein each occurrence of Rx independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the examples that are described herein.

3.7) The term "heteroaliphatic", as used herein, refers to aliphatic moieties that contain one or more oxygen, sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, F, Cl, Br, I, —OH, —$NO_2$, —CN, —$CF_3$, —$CH_2CF_3$, —$CHCl_2$, —$CH_2OH$, —$CH_2CH_2OH$, —$CH_2NH_2$, —$CH_2SO_2CH_3$, —C(O)Rx, —$CO_2$(Rx), —CON(Rx)$_2$, —OC(O)Rx, —$OCO_2$Rx, —OCON(Rx)$_2$, —N(Rx)$_2$, —S(O)$_2$Rx, —NRx(CO)Rx wherein each occurrence of Rx independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

3.8) The terms "halo" and "halogen" as used herein refer to an atom selected from fluorine, chlorine, bromine and iodine. The term "haloalkyl" denotes an alkyl group, as defined above, having one, two, or three halogen atoms attached thereto and is exemplified by such groups as chloromethyl, bromoethyl, trifluoromethyl, and the like.

3.9) The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic, heteroaliphatic, aryl, heteroaryl, arylalkyl, heteroarylalkyl, alkoxy, aryloxy, heteroalkoxy, heteroaryloxy, alkylthio, arylthio, heteroalkylthio, heteroarylthio, F, Cl, Br, I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)Rx, —CO$_2$(Rx), —CON(Rx)$_2$, —OC(O)Rx, —OCO$_2$Rx, —OCON(Rx)$_2$, —N(Rx)$_2$, —S(O)$_2$Rx, —NRx(CO)Rx wherein each occurrence of Rx independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the examples which are described herein.

The inventive compounds are useful as active agents in pharmaceutical compositions. In particular they may be used as a chemotherapeutic agent and for the treatment of cancer.

EXAMPLES

Synthetic Methodology

Prior to the present invention, only one synthesis of Iejimalide B (2) has been achieved (Fürstner A. et al. Angew. Chem. Int. Ed. 2006, 45, 5837-5842; Angew. Chem. 2006, 118, 5969-5974) which is hereby incorporated by reference in its entirety. Although novel and suitable for the synthesis of 2, this synthesis is not suitable for the rapid generation of (especially amino-functionalized) analoga. In one aspect, the present invention provides novel methods for the preparation of the natural compounds and analoga thereof. It will be appreciated that the figures shown in this invention depict exemplary synthesis approaches to a number of representative examples and that the methods described herein can be applied to the syntheses of a variety of analoga by the use of alternate starting materials. Furthermore the methods presented in this invention allow different modifications at a late stage in the sequence. Additionally, the reagents and starting materials are well known to those skilled in the art.

Figure 2:
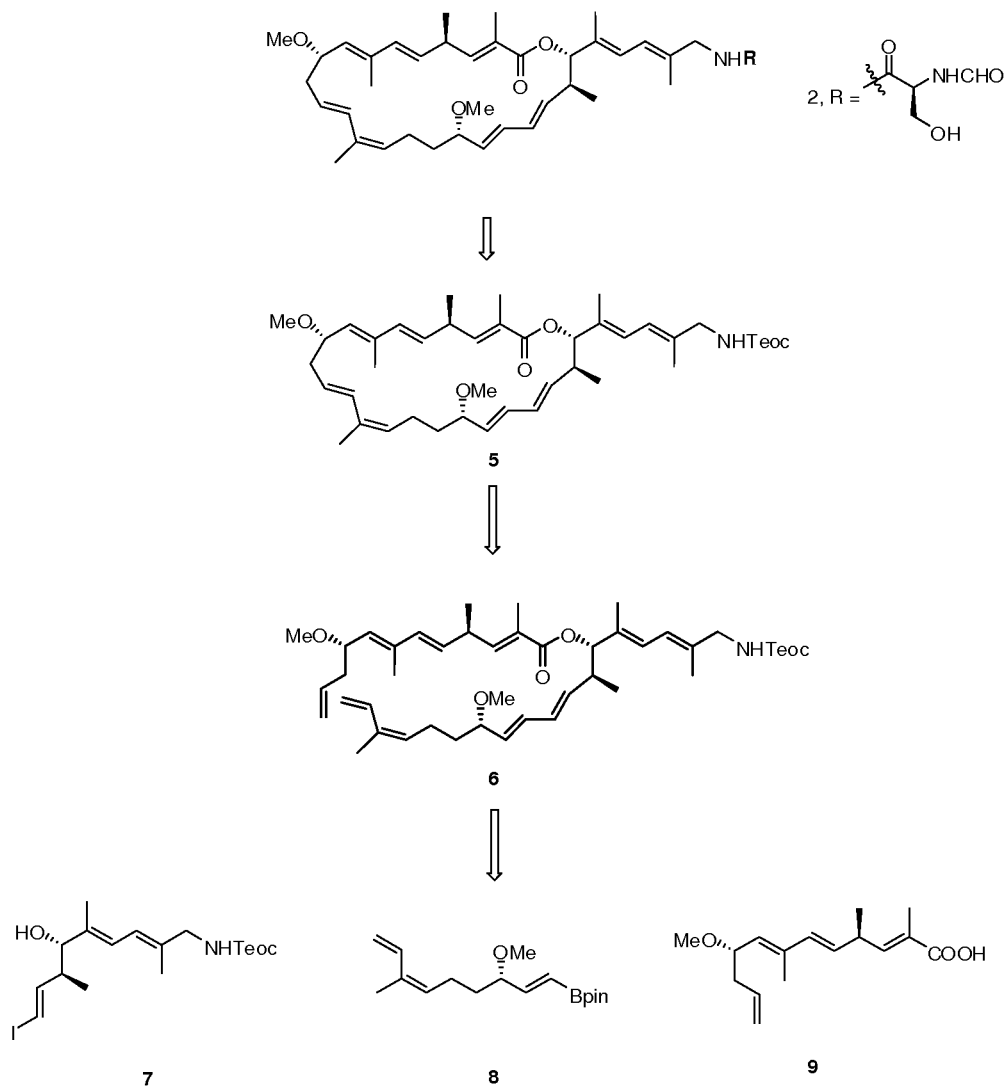
FIG. 2 shows the retrosynthetic strategy for a last stage modification of the aminofunctionality via synthesis of the Teoc-protected macrocycle 5.
Figure 3:
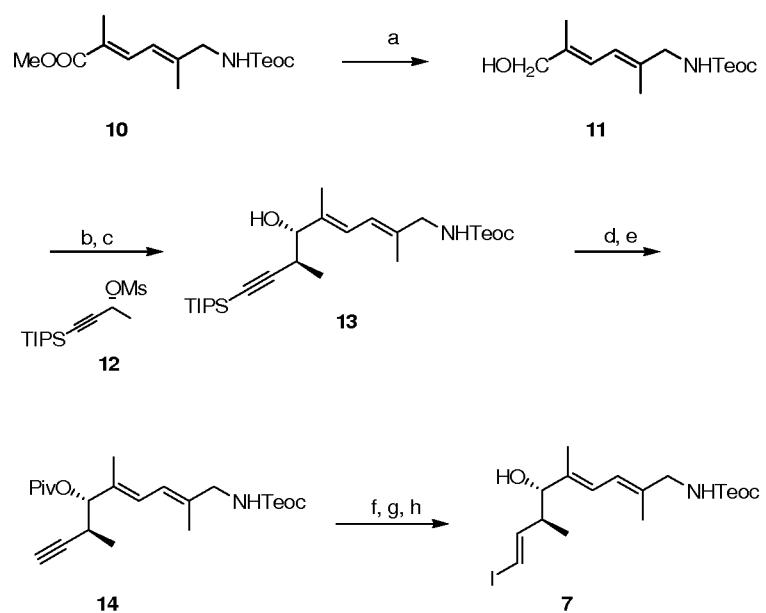
FIG. 3 depicts the synthesis of the Teoc-protected key-intermediate 7.
Figure 5:
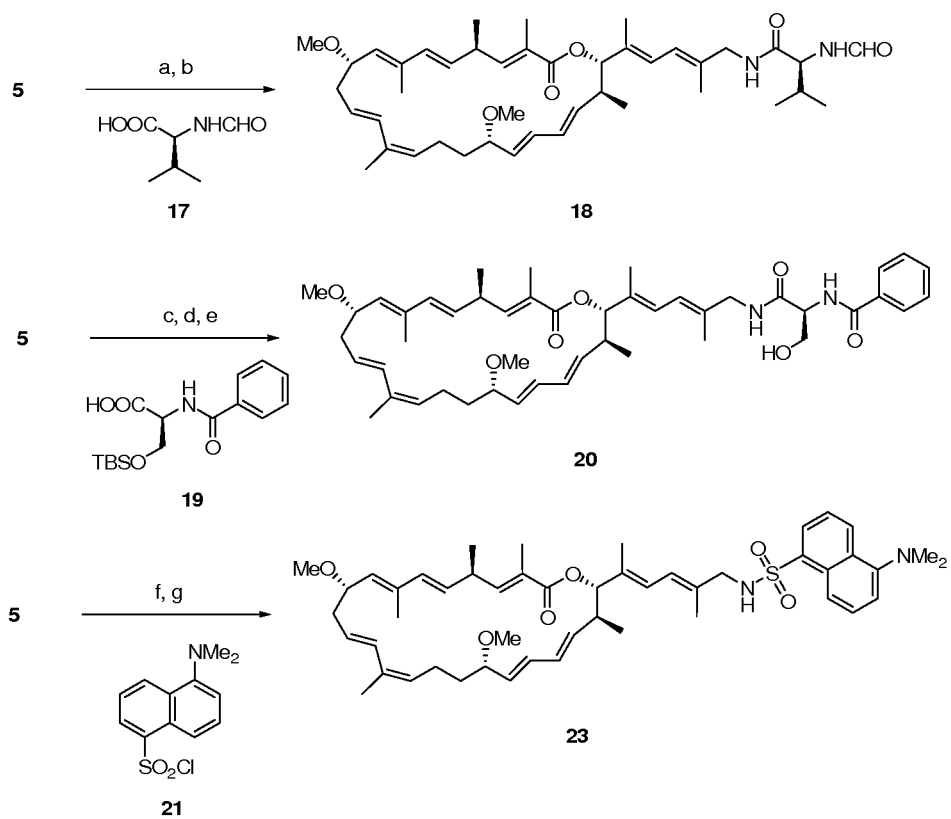
FIG. 5 depicts possible late stage modifications allowing the introduction of different aminoacids (i.e. 17 giving the macrocycle 18, and 19 giving the macrocycle 20) or other functional groups like 21 giving the fluorescent derivative 23.

As described in FIG. 2, a modified protecting group strategy has been developed, allowing the efficient generation of a variety of N-modified analoga of the Iejimalides as depicted in FIG. 5. As shown in FIG. 2, synthesis of the Teoc-protected macrocycle 5 from the 3 key-fragments 7, 8, and 9 allows the late stage introduction of different residues on the amino-functionality. As shown in FIG. 3, the sequence starts with the Teoc-protected ester 10 which, upon reduction to the alcohol 11, oxidation, and Pd-catalyzed alienation gives the anti-configurated alcohol 13 in 67%. The latter was converted to the iodine 7 in 4 steps in an overall yield of 63%.

Figure 4:
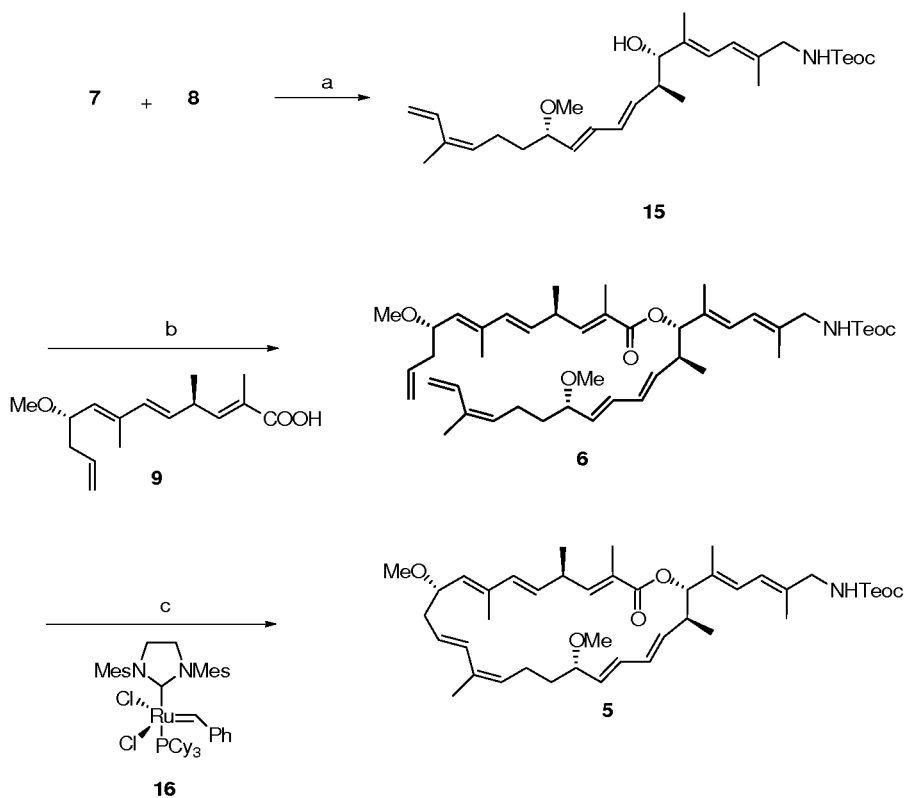
FIG. 4 depicts the synthesis of the Teoc-protected macrocycle 5.

As shown in FIG. 4, synthesis of 5 can be achieved upon Suzuki coupling of the iodine 7 with the Borane 8 in 70% yield, followed by an intermolecular esterification with the north fragment 9 (78%) and final ring closing metathesis (RCM) with Grubb's 2nd generation catalyst 16. This compound allows the introduction of a variety of residues on the final stage as shown in FIG. 5. First the Teoc-protecting group of 5 is cleaved with TBAF, followed by the direct coupling of either an aminoacid (i.e. 17 and 19) or an sulfonylchloride (e.g. 21) giving the N-functionalized analoga 18, 20, and 23.

Figure 6:
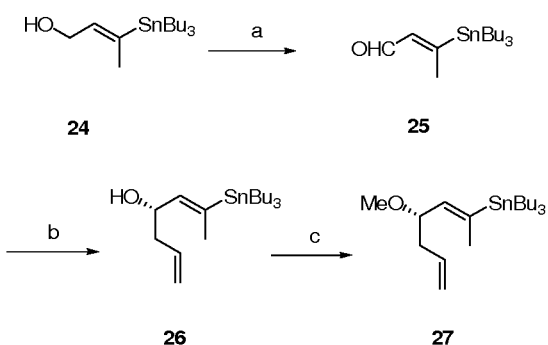
FIG. 6 depicts the synthesis of stannane 27.
Figure 7:
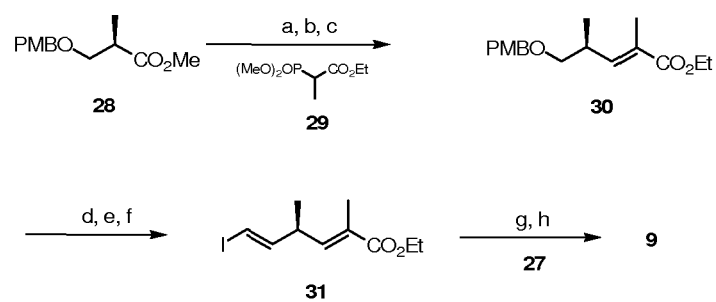
FIG. 7 shows the synthesis of the north fragment 9.

As the initially reported strategy for the synthesis of the north fragment 9 is rather long, improved methods for the stannane 27 well as for the iodine 31 were developed allowing the preparation of 9 in much more efficient and straight forward way. FIG. 6 shows the synthesis of 27 in just 3 steps from the alcohol 24 in an overall yield of 63% via a stereoselective allylation as the key step. The iodine 31 can be synthesized via an double-olefination strategy as shown in FIG. 7 (6 steps, 35% overall yield). Stille coupling of 31 and 27 followed by saponification gives the north fragment 9 in a straight forward manner.

Figure 8:
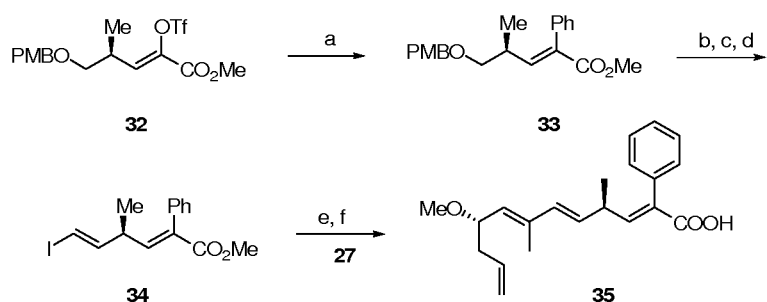
FIG. 8 illustrates the use of a Pd-catalyzed cross-coupling for the syntheses of the C2 arylated north fragment 35 and the C2-C3 saturated fragment 37.
Figure 8:
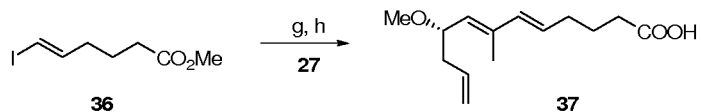
Figure 9:
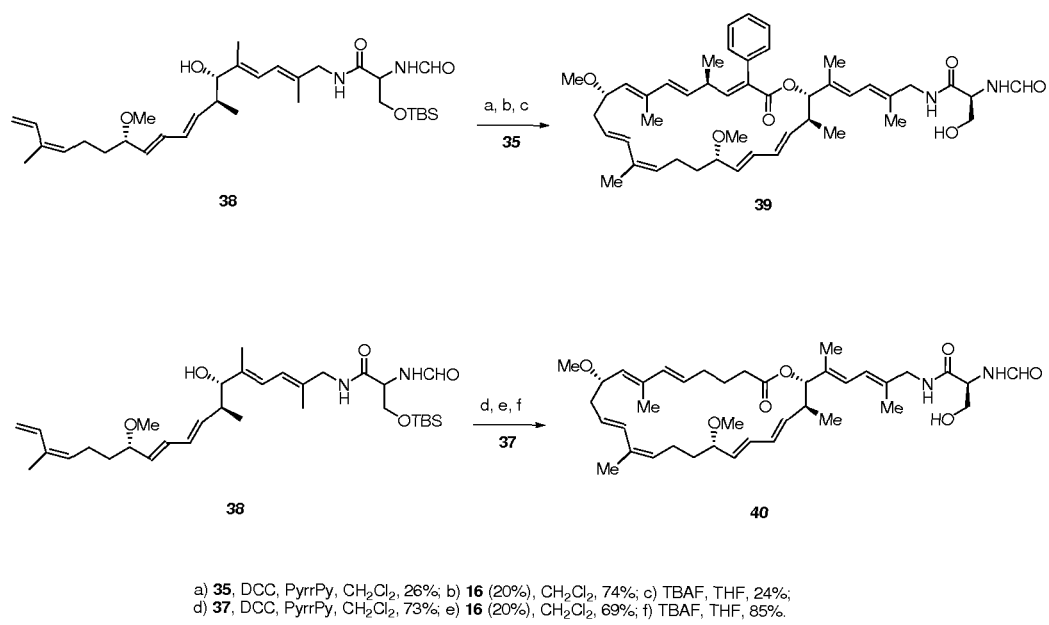
FIG. 9 depicts the syntheses of the C2-phenylsubstituted Iejimalide B analogue 39 and the C2-C4 simplified analogue 40.

An exemplary strategy for modifications at the C2 position of the macrocycle via a Pd-catalyzed cross-coupling of the triflate 32 with a variety of organo-zinc compounds (i.e. PhZnCl) is outlined in FIG. 8. Introduction of a phenyl substituent allowed the preparation of the PMB-protected alcohol 33 in 76% yield. Subsequent deprotection, oxidation, and Takai olefination gives the iodine 34 in 45% yield. Finally Stille coupling with 27 and saponification gives the C2-arylated north fragment 35. FIG. 8 also shows the suitability of this protocol for the synthesis of the C2-C4 simplified fragment 37. Both, 35 and 37, can be esterified with the south fragment 38 in the presence of DCC and 4-pyrrolidino-pyridine as shown in FIG. 9. Subsequent RCM and TBAF deprotection of the TBS-protected alcohol gives the corresponding the C2-phenyl substituted Iejimalide B analogue 39 as well as the C2-C4 simplified analogue 40 in moderate to good yields.

Figure 10:
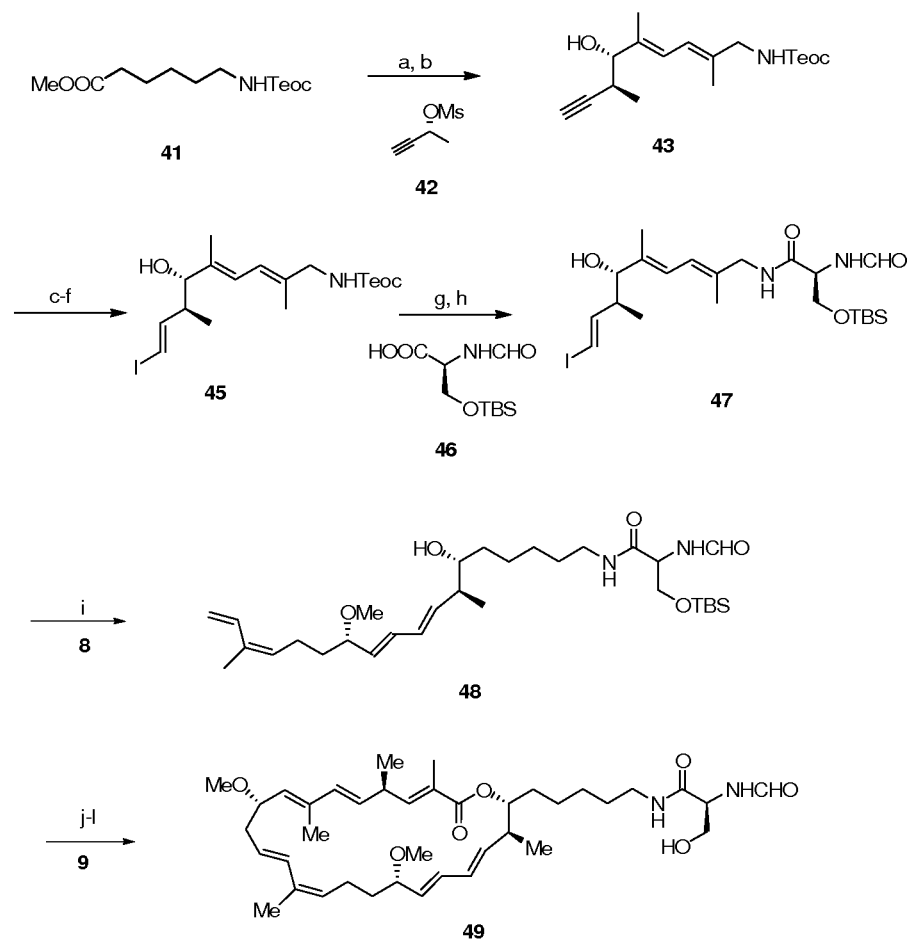
FIG. 10 depicts the syntheses of the side-chain simplified analogue 49.

FIG. 10 shows the applicability of this synthetic strategy for the synthesis of the side chain simplified analogue 49 starting from the ester 41 with the same methods already applied for the synthesis of the Teoc-macrocycle 5.

Equivalents

The representative examples that follow are intended to help illustrate the invention, and are not intended to, nor should they be construed to limit the scope of the invention. Indeed, various modification of the invention and many further embodiments thereof, in addition to those shown and described herein, will become apparent to those skilled in the art from the full contents of this document, including the examples which follow and the references to the scientific literature cited herein. It should further be appreciated that the contents of those cited references are incorporated herein by reference in order to illustrate the state of the art.

The following examples contain important additional information, exemplification, and guidance that can be adapted to the practice of this invention in its various embodiments and the equivalent thereof.

EXAMPLES

Example 1

Synthesis of the Teoc-Protected Macrocycle 5

Alcohol 11: A solution of 10 (770 mg, 2.46 mmol) in $CH_2Cl_2$ (17 mL) was cooled to −78° C. DIBAl-H (6.5 mL, 1M in hexane) was added dropwise and after 1 h at −78° C. EtOAc (2 mL) was added. After warming to room temperature, a saturated aqueous solution of Rochelle salt (about 10 mL) was added. The mixture was heated to 40° C. for 1 h, extracted with brine/EtOAc, and the combined organic layers dried over $Na_2SO_4$, and concentrated under vacuum. The crude product was chromatographed over silica gel (hexane/EtOAc 2:1) to give the 11 as a white solid (671 mg, 95%). $^1$H NMR (400 MHz, $CD_2Cl_2$): δ=6.25 (d, J=11.2 Hz, 1H), 6.15 (d, J=11.2 Hz, 1H), 4.80 (bs, 1H), 4.14 (t, J=8.4 Hz, 2H), 4.04 (s, 2H), 3.76 (d, J=6.1 Hz, 2H), 1.76 (s, 3H), 1.75 (s, 3H), 1.63 (s, 1H), 0.98 (t, J=8.4 Hz, 2H), 0.04 (s, 9H); $^{13}$C NMR (100 MHz, $CD_2Cl_2$): δ=157.0, 137.7, 135.2, 121.1, 120.3, 68.8, 63.3, 48.8, 18.0, 14.9, 14.2, −1.5; IR (film): ῦ=3331, 2954, 2914, 1689, 1531, 1346, 1246, 1130, 1063, 1001, 832, 690, 664 $cm^{-1}$; HRMS (ESI): m/z: calcd for $C_{14}H_{27}NO_3Si+Na$: 308.165245 $[M^++Na]$; found: 308.165153; elemental analysis calcd (%) for $C_{14}H_{27}NO_3Si$: C, 58.91; H, 9.53. found: C, 58.84; H, 9.57.

Alkyne 13: $MnO_2$ (8.5 g, 97 mmol) was added to a solution of 11 (827 mg, 2.9 mmol) in $CH_2Cl_2$ (30 mL) and stirred for 1 h. After filtration through celite and evaporation of the solvent the crude aldehyde 11a was obtained in quantitative yield and used directly for the alienation. To a solution of 12 (Marshall et al., JOC, 2006, 71, 4840) (1.32 g, 4.3 mmol) in THF (30 mL) at −78° C. were added $Pd(OAc)_2$ (33 mg, 0.147 mmol) and $PPh_3$ (40 mg, 0.152 mmol). After stirring for 5 min a solution of the in situ prepared crude aldehyde in THF (10 mL) was added followed by the dropwise addition of a solution of $ZnEt_2$ (8.7 mL, 1.0 M in hexanes). After stirring for 30 min, the solution was warmed up to −20° C. over a period of 1 h and stirred overnight. The solution was quenched with $NH_4Cl$ (sat.), the aqueous phase was extracted with EtOAc, the combined organic extracts were washed with brine, dried over $Na_2SO_4$ and concentrated under vacuum. The crude product (d.r.: 7.5:1 according to NMR) was chromatographed over silica gel (hexane/EtOAc 10:1→4:1) to give 13 as a colorless oil (1.02 g, 71%, ee=96.8%). $[\alpha]_D^{20}$=+47.5 (c=0.9, $CH_2Cl_2$); $^1$H NMR (400 MHz, $CD_2Cl_2$): δ=6.26 (d, J=11.2 Hz, 1H), 6.16 (d, J=11.2 Hz, 1H), 4.78 (bs, 1H), 4.15 (t, J=8.4 Hz, 2H), 3.85 (dd, J=7.0, 4.3 Hz, 1H), 3.76 (d, J=6.1 Hz, 2H), 2.75 (m, 1H), 2.29 (d, J=4.3 Hz, 1H), 1.75 (s, 3H), 1.72 (s, 3H), 1.13 (d, J=6.9 Hz, 3H), 1.05 (m, 21H), 0.98 (t, J=8.4 Hz, 2H), 0.04 (s, 9H); $^{13}$C NMR (100 MHz, $CD_2Cl_2$): δ=157.0, 136.9, 135.8, 123.1, 121.0, 110.3, 83.7, 81.0, 63.3, 48.8, 33.2, 18.8, 18.2, 18.1, 15.0, 12.2, 11.5, −1.4; IR (film): ῦ=3344, 2943, 2865, 2160, 1701, 1515, 1462, 1382, 1249, 1124, 1060, 1016, 858, 835, 675 $cm^{-1}$; HRMS (ESI): m/z: calcd for $C_{27}H_{51}NO_3Si_2+Na$: 516.329970 $[M^++Na]$; found: 516.330321; elemental analysis calcd (%) for $C_{27}H_{51}NO_3Si_2$: C, 65.66; H, 10.41. found: C, 65.76; H, 10.34.

Piv-protected alkyne 14: To an ice-cooled solution of 13 (501 mg, 1.01 mmol) in THF (20 mL) was added TBAF (1.2 mL, 1M in THF) in 4 portions over 2 h. After an additional 30 min the reaction was quenched with $H_2O$, the aqueous phase extracted with EtOAc, and the combined organic layers washed with brine, dried over $Na_2SO_4$, and concentrated under vacuum. The crude product was chromatographed over silica gel (hexane/EtOAc 4:1) to give a colorless oil (13a) (304 mg, 89%) which was dissolved in pyridine (3 mL) and DMAP (6 mg, 0.048 mmol) and pivaloylchloride (0.5 mL, 4.06 mmol). The mixture was stirred at rt for 20 h, extracted with brine/EtOAc, and the combined organic layers dried over $Na_2SO_4$, and concentrated under vacuum. The crude product was chromatographed over silica gel (hexane/EtOAc 10:1) to give 14 as a colorless oil (358 mg, 94%). $[\alpha]_D^{20}$=+21.4 (c=0.82, $CH_2Cl_2$); $^1$H NMR (400 MHz, $CD_2Cl_2$): δ=6.29 (d, J=11.3 Hz, 1H), 6.13 (d, J=11.3 Hz, 1H), 5.06 (d, J=7.7 Hz, 1H), 4.78 (bs, 1H), 4.14 (t, J=8.3 Hz, 2H), 3.76 (d, J=5.9 Hz, 2H), 2.82 (m, 1H), 2.08 (d, J=2.3 Hz, 1H), 1.76 (s, 3H), 1.74 (s, 3H), 1.21 (s, 9H), 1.11 (d, J=7.0 Hz, 3H), 0.98 (t, J=8.3 Hz, 2H), 0.04 (s, 9H); $^{13}$C NMR (100 MHz, $CD_2Cl_2$): δ=176.7, 156.4, 136.3, 133.8, 123.9, 119.8, 85.1, 80.4, 69.2, 62.7, 48.1, 38.6, 29.1, 26.7, 17.4, 17.1, 14.5, 12.1, −2.0; IR (film): ῦ=3314, 2970, 2955, 1725, 1520, 1366, 1248, 1231, 1217, 1149, 1061, 966, 942, 858, 835, 693 $cm^{-1}$; HRMS (ESI): m/z: calcd for $C_{23}H_{39}NO_4Si+Na$: 444.254058 $[M^++Na]$; found: 444.254501; elemental analysis calcd (%) for $C_{23}H_{39}NO_4Si$: C, 65.52; H, 9.32. found: C, 65.40; H, 9.28.

Iodine 7: To a solution of Schwartz's reagent (275 mg, 1.06 mmol) in THF (7 mL) in the dark was added a solution of 14 (260 mg, 0.616 mmol) in THF (7 mL). The mixture was stirred at rt for 45 min, cooled to 0° C. and a solution of iodine (270 mg, 1.06 mmol) in THF (5 mL) was added. After 5 min the reaction was quenched with aqueous $Na_2S_2O_3$ (sat.), stirred for 10 min, and extracted with brine/EtOAc. The combined organic layers were dried over $Na_2SO_4$ and concentrated under vacuum. The crude product was chromatographed over silica gel (hexane/EtOAc 10:1) giving the Piv-protected vinylic iodine 14a (273 mg, 81%). Superhydride (1.2 mL, 1M in THF) was added dropwise to an ice-cooled solution of 14a (195 mg, 0.355 mmol) in THF (20 mL). After stirring for 2 h at 0° C. the reaction was quenched with aqueous $NH_4Cl$ (sat.) and extracted with brine/EtOAc. The combined organic layers were dried over $Na_2SO_4$ and concentrated under vacuum. The crude product was chromatographed over silica gel (hexane/EtOAc 4:1) to give the product as a colorless oil (135 mg, 82%). $[\alpha]_D^{20}$=+28.1 (c=1.05, $CH_2Cl_2$); $^1$H NMR (300 MHz, $CD_2Cl_2$): δ=6.55 (dd, J=14.5, 8.3 Hz, 1H), 6.15 (m, 3H), 4.76 (bs, 1H), 4.15 (t, J=8.4 Hz, 2H), 3.78 (m, 3H), 2.40 (m, 1H), 1.94 (bs, 1H), 1.76 (s, 3H), 1.71 (s, 3H), 0.98 (t, J=8.4 Hz, 2H), 0.91 (d, J=6.8 Hz, 3H), 0.05 (s, 9H); $^{13}$C NMR (75 MHz, $CD_2Cl_2$): δ=157.0, 149.2, 137.7, 135.9, 123.6, 120.7, 81.3, 75.9, 63.3, 48.7, 44.8, 18.0, 16.5, 15.0, 12.0, −1.4; IR (film): ῦ=3337, 2966, 2887, 1694, 1519, 1466, 1394, 1248, 1171, 1060, 945, 856, 835, 776, 693 $cm^{-1}$; HRMS (ESI): m/z: calcd for $C_{18}H_{32}NO_3SiI+Na$: 488.108836 $[M^++Na]$; found: 488.108256; elemental analysis calcd (%) for $C_{18}H_{32}NO_3SiI$: C, 46.45; H, 6.93. found: C, 46.53; H, 7.06.

South fragment 15: To an Ar-flushed solution of 7 (50 mg, 0.107 mmol) and 8 (37 mg, 0.127 mmol) in DMF (2.5 mL) were added Ba(OH)$_2$.8H$_2$O (50 mg, 0.158 mmol) and PdCl$_2$(dppf) (12 mg, 0.016 mmol). The mixture was stirred at rt for 2 h, extracted with brine/EtOAc and the combined organic layers were dried over Na$_2$SO$_4$ and concentrated under vacuum. The crude product was chromatographed over silica gel (hexane/EtOAc 4:1) giving 15 (39 mg, 70%). $[\alpha]_D^{20}$=+26.6 (c=0.78, CH$_2$Cl$_2$); $^1$H NMR (400 MHz, CD$_2$Cl$_2$): δ=6.78 (ddd, J=17.3, 10.8, 0.8 Hz, 1H), 6.18 (m, 4H), 5.64 (m, 1H), 5.45 (m, 1H), 5.38 (m, 1H), 5.19 (dd, J=17.3, 0.8 Hz, 1H), 5.07 (m, 1H), 4.79 (bs, 1H), 4.15 (t, J=8.4 Hz, 2H), 3.75 (m, 3H), 3.52 (m, 1H), 3.21 (s, 3H), 2.38 (m, 1H), 2.20 (m, 2H), 1.81 (s, 3H), 1.75 (s, 3H), 1.73 (s, 3H), 1.63 (m, 1H), 1.49 (m, 1H), 0.98 (t, J=8.4 Hz, 2H), 0.90 (d, J=6.7 Hz, 3H), 0.04 (s, 9H); $^{13}$C NMR (100 MHz, CD$_2$Cl$_2$): δ=157.0, 138.1, 136.9, 135.6, 134.1, 133.2, 133.0, 132.8, 131.4, 131.0, 123.2, 121.0, 113.4, 82.1, 81.6, 63.3, 56.3, 48.8, 41.6, 36.0, 23.6, 19.9, 18.1, 17.3, 15.0, 11.9, −1.4; IR (film): ṽ=3457, 2925, 2855, 1737, 1516, 1448, 1366, 1229, 1216, 1099, 1060, 989, 858, 836, 776, 694 cm$^{-1}$; HRMS (ESI): m/z: calcd for C$_{29}$H$_{49}$NO$_4$Si+Na: 526.332305 [M$^+$+Na]; found: 526.332366; elemental analysis calcd (%) for C$_{29}$H$_{49}$NO$_4$Si: C, 69.14; H, 9.80. found: C, 68.96; H, 9.72.

Teoc-macrocycle 5: A solution of the 9 (20.0 mg, 0.0756 mmol) and 15 (19.0 mg, 0.0377 mmol) in CH$_2$Cl$_2$ (1.0 mL) was cooled to 0° C. Then EDC.HCl (14.5 mg, 0.0756 mmol) and 4-pyrrolidino-pyridine (14.5 mg, 0.0983 mmol) were sequentially added. The mixture was warmed to rt within 1 h and stirred for 48 h. Then, it was cooled again to 0° C. and EDC.HCl (2.2 mg, 0.0115 mmol) and 4-pyrrolidino-pyridine (1.7 mg, 0.0115 mmol) were added. After another 48 h no alcohol 15 was left and the mixture was diluted with EtOAc, filtered over celite, and directly submitted to column chromatography (silica gel, gradient hexane/EtOAc 20:1→2:1) giving 6a colorless oil (22 mg, 78%). To a solution of 6 (9.0 mg, 0.0116 mmol) in CH$_2$Cl$_2$ (20 mL) was added Grubbs 2$^{nd}$ generation catalyst (16) (1 mg, 0.0012 mmol) and the mixture stirred at rt. After 24 h another portion of 16 (0.5 mg, 0.0006 mmol) was added as well as after 48 h. After 72 h the reaction was quenched with ethylvinylether (50 μL) and stirred for 1 hour. After evaporation of the solvent, column chromatography (silica gel, gradient hexane/EtOAc 12:1→8:1) gave the desired macrocycle 5 as a brown solid (6.5 mg, 78%). $[\alpha]_D^{20}$=+5.0 (c=0.10, CH$_2$Cl$_2$); $^1$H NMR (400 MHz, CD$_2$Cl$_2$): δ=6.57 (dd, J=10.3, 1.4 Hz, 1H), 6.46 (d, J=15.7 Hz, 1H), 6.29 (d, J=11.2 Hz, 1H), 6.12 (dc, J=11.2, 1.2 Hz, 1H), 6.04 (dd, J=14.3, 10.5 Hz, 1H), 5.97 (dd, J=14.5, 10.5 Hz, 1H), 5.89 (d, J=15.5 Hz, 1H), 5.52 (ddd, J=15.5, 9.7, 4.6 Hz, 1H), 5.48 (dd, J=15.5, 9.0 Hz, 1H), 5.38 (dd, J=14.1, 7.9 Hz, 1H), 5.36 (dd, J=14.5, 9.7 Hz, 1H), 5.18 (dd, J=10.5, 5.8 Hz, 1H), 5.09 (d, J=10.1 Hz, 1H), 5.08 (d, J=9.5 Hz, 1H), 4.76 (brs, 1H), 4.14 (dd, J=8.5, 8.3 Hz, 2H), 4.16-4.09 (m, 1H), 3.76 (d, J=6.0 Hz, 2H), 3.29-3.23 (m, 1H), 3.21 (s, 3H), 3.18-3.12 (m, 1H), 2.95 (s, 3H), 2.65-2.61 (m, 1H), 2.58-2.48 (m, 2H), 2.29 (dt, J=13.5, 10.1 Hz, 1H), 1.90-1.86 (m, 1H), 1.78 (s, 3H), 1.77 (s, 3H), 1.77 (s, 3H), 1.76 (s, 3H), 1.74 (d, J=1.0 Hz, 3H), 1.63-1.56 (m, 1H), 1.33-1.25 (m, 1H), 1.03 (d, J=6.7 Hz, 3H), 0.98 (dd, J=8.5, 8.4 Hz, 2H), 0.91 (d, J=6.7 Hz, 3H); $^{13}$C NMR (150 MHz, CD$_2$Cl$_2$): δ=167.57, 156.97, 145.63, 137.12, 136.88, 136.23, 133.87, 133.81, 133.75, 133.34, 132.40, 132.34, 132.06, 131.23, 129.77, 128.80, 125.96, 125.61, 125.38, 120.59, 83.32, 79.85, 77.04, 63.31, 56.48, 55.87, 48.75, 40.98, 38.33, 35.30, 23.23, 21.49, 20.78, 18.06, 16.81, 15.08, 13.15, 12.10, 12.07, 1.149, −1.42; IR (film): ṽ=2927, 1712, 1514, 1455, 1251, 1100, 989, 965, 836 cm$^{-1}$; HRMS (ESI): m/z: calcd for C$_{43}$H$_{67}$NO$_6$+Na: 744.4627, [M$^+$+Na]; found: 744.4629;

Example 2

Late Stage Modifications on the Aminofunctionality

N-Formyl-valine-iejimalide B (18): The Teoc-macrocycle 5 (3.0 mg, 0.0042 mmol) was dissolved in THF (0.1 mL), cooled to 0° C., and TBAF (17 μL, 1M in THF) was added dropwise. The mixture was allowed to warm to rt over 1 h and stirred for 36 h. Extraction with EtOAc/NH$_4$Cl, drying over MgSO$_4$, and concentration under vacuum gave the crude free amine which was dissolved in CH$_2$Cl$_2$ (0.1 mL). 17 (0.8 mg, 0.0054 mmol), HOAt (0.70 mg, 0.0050 mmol), and collidine (1.7 μL, 0.013 mmol) were added, and the solution cooled to 0° C. EDC.HCl (1.2 mg, 0.0063 mmol) was added and the mixture allowed to warm up to rt over 1 h and stirred for 20 h. Extraction with EtOAc/brine, drying over MgSO$_4$, and concentration under vacuum afforded a crude mixture which was purified by column chromatography over silica gel (gradient hexane/EtOAc 5:1→1:2) to give the product (3 mg, 100%, about 10% isomers due to TBAF deprotection). Further purification by preparative HPLC afforded 18 as a colorless oil (2.6 mg, 75%). $[\alpha]_D^{20}$=−5.0 (c=0.12, CH$_2$Cl$_2$); $^1$H NMR (600 MHz, C$_6$D$_6$): δ=7.68 (s, 1H), 7.01 (d, J=11.4 Hz, 1H), 6.81 (d, J=15.6 Hz, 1H), 6.48 (d, J=11.2 Hz, 1H), 6.11 (d, J=11.2 Hz, 1H), 6.01 (dd, J=15.0, 10.5 Hz, 1H), 5.79 (d, J=15.7 Hz, 1H), 5.75 (dd, J=15.2, 10.5 Hz, 1H), 5.60-5.57 (m, 1H), 5.54 (d, J=10.2 Hz, 1H), 5.48-5.43 (m, 2H), 5.35 (dd, J=15.2, 9.5 Hz, 1H), 5.27-5.23 (m, 2H), 5.20-5.15 (m, 2H), 4.16 (dd, J=7.9, 7.9 Hz, 1H), 3.98 (td, J=9.5, 1.6 Hz, 1H), 3.74 (dd, J=15.5, 6.3 Hz, 1H), 3.54 (dd, J=15.5, 5.6 Hz, 1H), 3.39-3.36 (m, 1H), 3.14 (s, 3H), 3.13 (s, 3H), 2.99-2.88 (m, 2H), 2.86-2.80 (m, 1H), 2.56-2.48 (m, 2H), 1.94 (s, 3H), 1.90-1.86 (m, 2H), 1.84 (s, 3H), 1.82 (s, 3H), 1.79-1.71 (m, 1H), 1.49 (s, 6H), 1.36-1.17 (m, 1H), 0.88-0.85 (m, 9H), 0.78 (d, J=6.8 Hz, 3H); $^{13}$C NMR (150 MHz, C$_6$D$_6$): δ=170.35, 167.10, 160.44, 145.86, 136.91, 135.99, 135.95, 133.88, 133.68, 133.32, 133.08, 132.52, 131.78, 131.74, 129.99, 129.17, 125.98, 125.93, 125.54, 121.06, 83.10, 79.50, 76.86, 57.20, 56.35, 55.51, 46.67, 41.61, 41.40, 38.48, 35.28, 31.31, 23.32, 21.35, 21.23, 19.46, 18.11, 16.92, 14.95, 12.98, 12.17, 12.10; IR (film): ṽ=3287, 2959, 2924, 2854, 1651 (br), 1547, 1461, 1377, 1259, 1217, 1102, 965, 801, 744 cm$^{-1}$; HRMS (ESI): m/z: calcd for C$_{43}$H$_{64}$N$_2$O$_6$+Na: 727.4663 [M$^+$+Na]; found: 727.4657.

N-Benzoyl-serine-iejimalide B (20): The Teoc-macrocycle (8 mg, 0.0113 mmol) was dissolved in THF (0.4 mL), cooled to 0° C., and TBAF (45 μL, 1M in THF) was added dropwise. The mixture was allowed to warm to rt over 3 h and stirred for 20 h. Extraction with EtOAc/brine, drying over MgSO$_4$, and concentration under vacuum gave the crude free amine which was dissolved in CH$_2$Cl$_2$ (1.5 ml). 19 (7.5 mg, 0.023 mmol), HOBt (2.8 mg, 0.01 mmol), and NMM (4 μL, 0.036 mmol) were added, and the solution cooled to 0° C. EDC.HCl (4 mg, 0.02 mmol) was added and the mixture allowed to warm up to rt over 1 h and stirred for 20 h. The mixture was directly purified by column chromatography over silica gel (hexane/EtOAc 2:1) to give the O-TBS protected 20. To an ice-cooled solution of the protected 20 in THF (0.2 mL) was added TBAF (4 μL, 1M in THF) and the solution stirred at 0° C. for 20 min. The mixture was directly submitted to column chromatography (silica gel, hexane/EtOAc 1:1) and further purified by preparative HPLC to give 20 as a white solid (1.5 mg, 17%). $[\alpha]_D^{20}$=+4 (c=0.16, CH$_2$Cl$_2$); $^1$H NMR (600 MHz, CD$_2$Cl$_2$): δ=7.82 (m, 2H), 7.55 (m, 1H), 7.47 (m, 2H), 7.27 (d, J=6.6 Hz, 1H), 6.92 (t, J=5.6 Hz, 1H), 6.57 (m, 1H), 6.45 (d, J=15.2 Hz, 1H), 6.27 (d, J=10.9 Hz, 1H), 6.13 (m, 1H), 6.06-5.94 (m, 2H), 5.89 (d, J=15.2 Hz, 1H), 5.55-5.45 (m, 2H), 5.40-4.34 (m, 2H), 5.18 (m, 1H), 5.08 (m, 2H), 4.60 (m, 1H), 4.23 (m, 1H), 4.11 (dt, J=9.9, 2.2 Hz, 1H), 3.95-3.83 (m, 2H), 3.74 (m, 1H), 3.27 (m, 1H), 3.21 (s, 3H), 3.20 (m, 1H), 3.15 (m, 1H), 2.95 (s, 3H), 2.63 (m, 1H), 2.55-2.47 (m, 2H), 2.29 (m, 1H), 1.88 (m, 1H), 1.77 (s, 3H), 1.76 (s, 3H), 1.75 (s, 3H), 1.74 (s, 3H), 1.70 (s, 3H), 1.61-1.54 (m, 1H), 1.33-1.25 (m, 1H), 1.04 (d, J=6.8 Hz, 3H), 0.90 (d, J=6.8 Hz, 3H); $^{13}$C NMR (125 MHz, CD$_2$Cl$_2$): δ=171.3, 168.2, 167.5, 145.6, 137.1, 136.1, 135.6, 134.2, 133.8, 133.7, 133.7, 133.3, 132.4 (2×), 132.3, 132.1, 131.2, 129.8, 129.0, 128.8, 127.5, 126.0, 125.4, 125.3, 121.0, 83.1, 80.0, 77.1, 63.1, 56.5, 55.9, 55.4, 47.0, 41.0, 40.8, 38.2, 35.3, 23.2, 21.5, 20.8, 16.8, 15.2, 13.2, 12.1, 12.0; IR (film): ῦ=3333, 2925, 1710, 1643, 1529, 1448, 1257, 1216, 1104, 989, 964, 744, 712 cm$^{-1}$; HRMS (ESI): m/z: calcd for C$_{47}$H$_{64}$N$_2$O$_7$+Na: 791.460572 [M$^+$+Na]; found: 791.460821.

Example 3

Synthesis of C2-C4 Modified Analoga

C2-C4 simplified analogue 40: A solution of 37 (8 mg, 0.0336 mmol) and 38 (20 mg, 0.0338 mmol) in CH$_2$Cl$_2$ (0.5 mL) was cooled to 0° C. Then the 4-pyrrolidino-pyridine (0.8 mg, 0.0054 mmol) and the DCC (7 mg, 0.034 mmol) were added. The mixture was warmed to rt within 1 h and stirred for 40 h. After dilution with EtOAc, the suspension was filtered over celite and directly submitted to column chromatography (silica gel, hexane/EtOAc 1:1) giving the ester 40a (20 mg, 73%). To a solution of this material (6.0 mg, 0.0074 mmol) in CH$_2$Cl$_2$ (14 mL) was added 16 (0.8 mg, 0.00074 mmol) and the mixture stirred at rt. After 24 h another portion of 16 (0.5 mg, 0.0006 mmol) was added. After 24 h the reaction was quenched with ethylvinylether (50 μL) and stirred for 1 hour. After evaporation of the solvent, column chromatography (silica gel, gradient hexane/EtOAc 3:1→1:1) gave the O-TBS protected 40b as a colorless oil (4.0 mg, 69%). To an ice-cooled solution of the protected starting material (11 mg, 0.0014 mmol) in THF (0.25 mL) was added TBAF (14.1 μL, 1M in THF) and the mixture stirred at 0° C. for 10 min. The mixture was directly submitted to column chromatography (silica gel, gradient hexane/EtOAc 1:1→0:1+3% MeOH) to give 40 as a colorless oil (8 mg, 85%). [α]$_D^{20}$=−1.0 (c=0.4, CH$_2$Cl$_2$); $^1$H NMR (400 MHz, CD$_2$Cl$_2$): δ=8.26 (s, 1H), 6.76 (d, J=6.6 Hz, 1H), 6.70 (t, J=5.5 Hz, 1H), 6.40 (d, J=15.6 Hz, 1H), 6.26 (d, J=11.4 Hz, 1H), 6.12 (d, J=11.4 Hz, 1H), 6.10-5.98 (m, 2H), 5.91 (d, J=15.6 Hz, 1H), 5.62-5.40 (m, 4H), 5.23 (dd, J=9.3, 7.2 Hz, 1H), 5.07 (d, J=11.4 Hz, 1H), 5.04 (d, J=9.9 Hz, 1H), 4.50-4.46 (m, 1H), 4.16-4.10 (m, 2H), 3.99-3.82 (m, 2H), 3.65 (ddd, J=11.3, 8.5, 5.0 Hz, 1H), 3.34-3.29 (m, 1H), 3.27-3.18 (m, 1H), 3.23 (s, 3H), 3.13 (s, 3H), 3.12-3.10 (m, 1H), 2.63-2.52 (m, 2H), 2.48-2.38 (m, 1H), 2.31-2.21 (m, 3H), 2.05-1.92 (m, 3H), 1.78 (s, 3H), 1.75 (brs, 6H), 1.72 (s, 3H), 1.34-1.23 (m, 1H), 0.90 (d, J=6.7 Hz, 3H); $^{13}$C NMR (75 MHz, CD$_2$Cl$_2$): δ=173.1, 170.7, 161.9, 137.0, 136.4, 135.5, 135.0, 134.5, 133.8, 133.3, 132.2, 131.2, 130.8, 129.9, 129.1, 129.0, 125.4, 125.2, 121.0, 83.2, 80.2, 77.3, 62.8, 56.5, 56.1, 53.0, 47.1, 40.5, 39.9, 35.8, 35.0, 33.4, 26.2, 23.3, 20.7, 17.5, 15.2, 13.4, 12.3; IR (film): ῦ=3301, 2927, 1727, 1656, 1535, 1449, 1378, 1197, 1146, 1102, 990, 965, 866 cm$^{-1}$; HRMS (ESI): m/z: calcd for C$_{39}$H$_{58}$N$_2$O$_6$+Na: 689.4139 [M$^+$+Na]; found: 689.4136.

C2-Phenyl-Iejimalide B 39: A solution of 35 (5 mg, 0.0153 mmol) and 38 (9 mg, 0.0152 mmol) in CH$_2$Cl$_2$ (0.15 mL) was cooled to 0° C. Then the 4-pyrrolidino-pyridine (0.4 mg, 0.0027 mmol) and the DCC (3.3 mg, 0.016 mmol) were added. The mixture was warmed to rt within 1 h and stirred for 24 h. After the addition of more 4-pyrrolidino-pyridine (0.2 mg, 0.00135 mmol) and stirring for additional 24 h the mixture was diluted with EtOAc, the suspension filtered over celite, and directly submitted to column chromatography (silica gel, hexane/EtOAc 1:1) giving the ester (3.5 mg, 26%) as a mixture of isomers (about 70-80% of the main isomer) and recovered alcohol (3 mg, 66% conversion). To a solution of this ester (4 mg, 0.0045 mmol, 3.5:1 mixture of isomers) in CH$_2$Cl$_2$ (7 mL) was added Grubb's 2$^{nd}$ generation catalyst (16) (0.4 mg, 0.00044 mmol) and the mixture stirred at rt. After 24 h another portion of catalyst (0.2 mg, 0.00022 mmol) was added as well as after 48 h. After 72 h the reaction was quenched with ethylvinylether (20 μL) and stirred for 15 min. After evaporation of the solvent, column chromatography (silica gel, hexane/EtOAc 1:1) gave the O-TBS-protected 39 (2.9 mg, 74%) which was dissolved in THF (0.2 mL), cooled to 0° C., and TBAF (3.3 μL, 1M in THF) was added. After 10 min the mixture was directly submitted to column chromatography (silica gel, hexane/EtOAc 1:1) to give the product as a mixture of isomers (1.5 mg, 60%, about 60-70% of the main isomer). Further purification by preparative HPLC allowed the isolation of the main isomer 39 (0.6 mg, 24%) IR (film): ῦ=3304, 2924, 2856, 1733, 1658, 1456, 1260, 1148, 1100, 989, 965, 803 cm$^{-1}$; HRMS (ESI): m/z: calcd for C$_{46}$H$_{62}$N$_2$O$_7$+Na: 777.444919 [M$^+$+Na]; found: 777.444225.

Example 4

Synthesis of Side-Chain Modified Analoga

Saturated side-chain analogue 49: A solution of 9 (16.0 mg, 0.0605 mmol) in CH$_2$Cl$_2$ (0.2 mL) was cooled to 0° C. Then 4-pyrrolidino-pyridine (1.2 mg, 0.0082 mmol) and DCC (11.3 mg, 0.0547 mmol) were added. After stirring at rt for 10 min the resulting suspension was cooled to 0° C. and a solution of 48 (31.0 mg, 0.0547 mmol) in CH$_2$Cl$_2$ (0.15 mL) was added. The mixture was warmed to rt within 1 h and stirred for 36 h after which it was cooled to 0° C. again and more 4-pyrrolidino-pyridine (1.2 mg, 0.0082 mmol), and DCC (5.0 mg, 0.0243 mmol) were added. After another 48 h the mixture was diluted with EtOAc, filtered over celite, and directly submitted to column chromatography (silica gel, gradient hexane/EtOAc 15:1→0:1) giving ester 49a as a colorless oil (33 mg, 74%, 100% based on recovered alcohol). To a solution of this material (11.0 mg, 0.0136 mmol) in CH$_2$Cl$_2$ (25 mL) was added 16 (1.10 mg, 0.00131 mmol) and the mixture stirred at rt. After 24 h another portion of 16 (0.5 mg, 0.0006 mmol) was added. After 24 h the reaction was quenched with ethylvinylether (50 μL) and stirred for 1 hour. After evaporation of the solvent, column chromatography (silica gel, gradient hexane/EtOAc 1:1→1:3) gave the O-TBS protected 49b as a colorless oil (8.7 mg, 55%). To an ice-cooled solution of 49b (15.0 mg, 0.0192 mmol) in THF (0.25 mL) was added TBAF (18.5 μL, 1M in THF) and the mixture stirred at 0° C. for 10 min. The mixture was directly submitted to column chromatography (silica gel, gradient hexane/EtOAc 1:1→0:1+3% MeOH) to give 49 as a colorless oil (8.4 mg, 66%). [α]$_D^{20}$=−11.0 (c=0.08, CH$_2$Cl$_2$); $^1$H NMR (400 MHz, CD$_2$Cl$_2$): δ=8.27 (s, 1H), 6.79 (brs, 1H), 6.59 (brs, 1H), 6.51 (dd, J=10.0, 1.2 Hz, 1H), 6.46 (d, J=15.5 Hz, 1H), 6.00-5.90 (m, 2H), 5.87 (d, J=15.4 Hz, 1H), 5.55 (m, 2H), 5.38-5.33 (m, 2H), 5.16 (dd, J=11.0, 5.6 Hz, 1H), 5.07 (d, J=9.4 Hz, 1H), 4.79 (td, J=9.2, 2.7 Hz, 1H), 4.46-4.42 (m, 1H), 4.11 (ddd, J=10.1, 9.6, 2.6 Hz, 1H), 4.06 (ddd, J=11.1, 4.1, 3.5 Hz, 1H), 3.65-3.58 (m, 1H), 3.29-3.15 (m, 4H), 3.21 (s, 3H), 2.93 (s, 3H), 2.66-2.51 (m, 2H), 2.34-2.23 (m, 2H), 1.87-1.79 (m, 1H), 1.77 (s, 3H), 1.75 (s, 3H), 1.74 (s, 3H), 1.61-1.27 (m, 10H), 1.06 (d, J=6.7 Hz, 3H), 1.01 (d, J=6.7 Hz, 3H); $^{13}$C NMR (75 MHz, CD$_2$Cl$_2$): δ=170.6, 168.7, 161.8, 145.7, 137.1, 136.5, 133.7, 133.5, 133.4, 132.6, 132.4, 132.0, 130.8, 129.8, 128.8, 125.9, 125.4, 79.9, 77.1, 77.1, 63.0, 56.4, 55.9, 52.9, 43.6, 41.0, 39.7, 38.3, 35.3, 32.4, 29.6, 26.3, 25.2, 23.2, 21.7, 20.8, 17.3, 13.2, 12.1; IR (film): ύ=3324, 2928, 1649, 1545, 1450, 1381, 1259, 1218, 1103, 990, 964, 745 cm$^{-1}$; HRMS (ESI): m/z: calcd for C$_{39}$H$_{60}$N$_2$O$_7$+Na: 691.4296 [M$^+$+Na]; found: 691.4293.

The invention claimed is:

1. A compound having the structure:

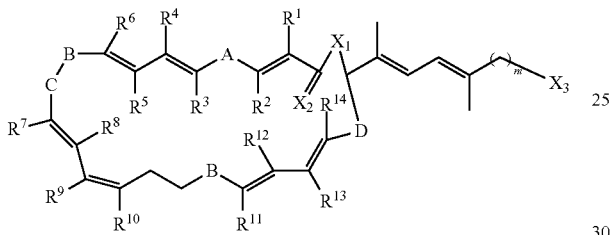

wherein:

m=0-20;

R$^{1-14}$ independently represent hydrogen or alkyl;

X$_1$ is O;

X$_2$ is O;

X$_3$ is NHR$_h$, wherein R$_h$ is a natural or unnatural amino acid residue bound to NH of X$_3$ by amide linkage, the unnatural amino acid residue being selected from the group consisting of:

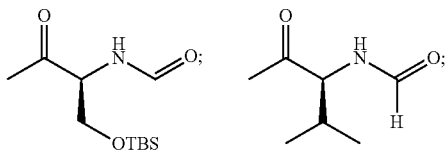

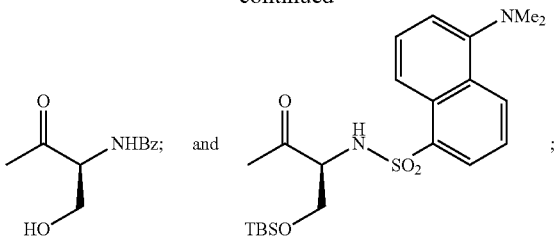

A, C and D independently represent CH$_2$, CHR$_j$ or C(R$_j$)$_2$, wherein each occurrence of R$_j$ is hydrogen or alkyl; and each B independently represents CHR$_1$, wherein each R$_1$ is independently OR$_m$, wherein R$_m$ is independently hydrogen or alkyl;

with the proviso that the following compounds are excluded: compounds wherein the following occur simultaneously: X$_1$ is O (S configuration), X$_2$ is O, R$_1$=Me, R$_2$=H, A=CHCH$_3$ (R configuration), R$_3$=R$_4$=H, R$_5$=Me, R$_6$=H, B is CHOMe (S configuration), C is CH$_2$, R$_7$=R$_8$=H, R$_9$=Me, R$_{10}$=H, B is CHOMe (S configuration), R$_{11}$=R$_{12}$=R$_{13}$=R$_{14}$=H, D is CHCH$_3$ (S configuration), m=1, and X$_3$ is:

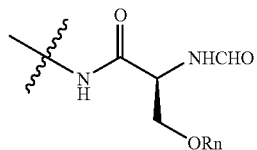

wherein Rn=TBS.

2. The compound having the structure:

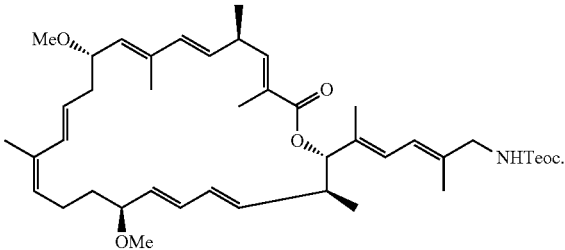

3. The compound according to claim 1, which has the structure:

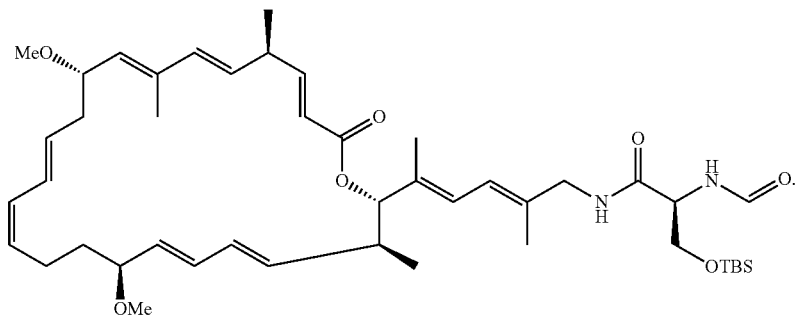 [SMILES: CO[C@@H]1/C=C(C)/C=C/[C@@H](C)/C=C/C(=O)O[C@H](/C(C)=C/C=C(\C)CNC(=O)[C@H](CO[Si](C)(C)C(C)(C)C)NC=O)[C@@H](C)/C=C/C=C/[C@@H](OC)CC/C=C\C=C\C1]

4. The compound according to claim 1, which has the structure:
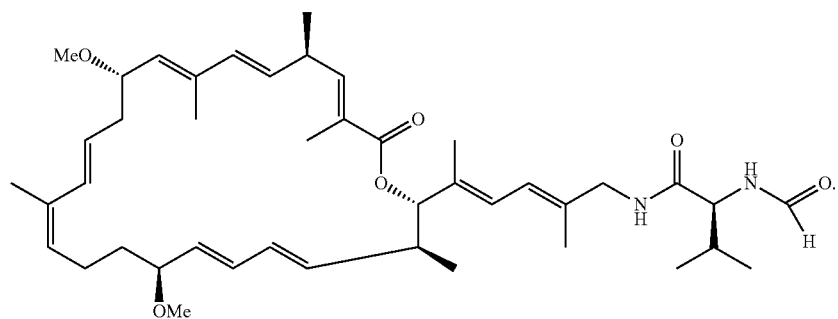 [SMILES: CO[C@@H]1/C=C(C)/C=C/[C@@H](C)/C=C(\C)C(=O)O[C@H](/C(C)=C/C=C(\C)CNC(=O)[C@@H](NC=O)C(C)C)[C@@H](C)/C=C/C=C/[C@@H](OC)CC/C=C(C)\C=C\C1]
5. The compound according to claim 1, which has the structure:
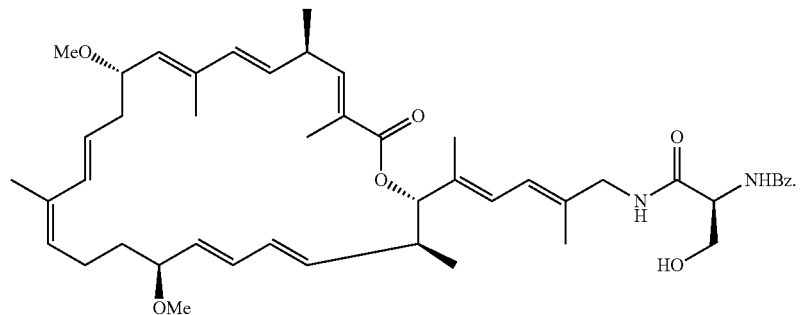
6. The compound according to claim 1, which has the structure:
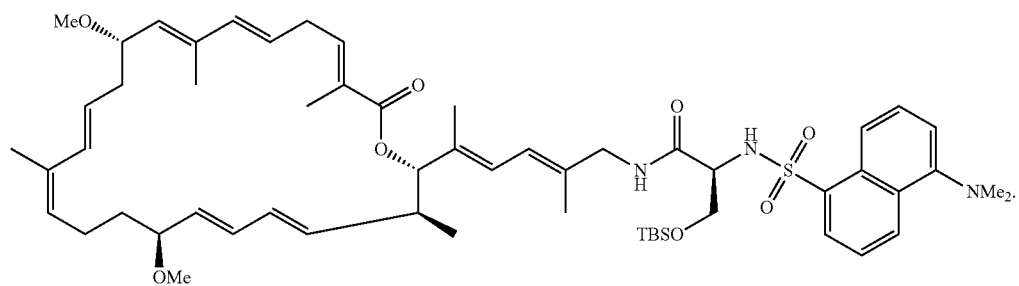 [SMILES: CO[C@@H]1/C=C(C)/C=C/C/C=C(\C)C(=O)O[C@H](/C(C)=C/C=C(\C)CNC(=O)[C@H](CO[Si](C)(C)C(C)(C)C)NS(=O)(=O)c2cccc3c(N(C)C)cccc23)[C@@H](C)/C=C/C=C/[C@@H](OC)CC/C=C(C)\C=C\C1]
7. A pharmaceutical composition comprising at least one compound according to claim 1.
* * * * *